United States Patent [19]
Sariola et al.

[11] Patent Number: 5,882,923
[45] Date of Patent: Mar. 16, 1999

[54] GLIAL CELL LINE-DERIVED NEUROTROPHIC FACTOR REGULATION OF URETERIC BUDDING AND GROWTH

[76] Inventors: Hannu Sariola, Oravatie 15 FIN-00800; Kirsi Sainio, Maasälväntie 10 C 10 FIN-00710, both of Helsinki; Petro Suvanto, Neilikkatie 4a4 FIN-01300, Vantaa; Urmas Arumae, Niittykatu 3d53 FIN-02200, Helsinki; Maria Lindahl, Haukiverkko 17 as. 4 FIN-02170, Espoo; Mart Saarma, Kulosaaren Puistotie 36B 15, FIN-00570, Helsinki, all of Finland

[21] Appl. No.: 884,176

[22] Filed: Jun. 27, 1997

Related U.S. Application Data

[60] Provisional application No. 60/021,964 Jun. 27, 1996.
[51] Int. Cl.$^6$ .............................. C12N 5/00; C12N 5/02; C12N 5/08; A61K 38/18
[52] U.S. Cl. ..................... 435/325; 435/368; 435/369; 435/375; 435/384; 514/2
[58] Field of Search .................. 514/2, 12, 22; 435/325, 384, 368, 369, 375

[56] References Cited

PUBLICATIONS

Pitchel et al., "GNDF is Required for Kidney Development and Enteric Innervation," *Cold Spring Harbor Sym. Quant. Bio.*, 1996, 61, 445–457.

Moore et al., "Renal and Neuronal Abnormalities in Mice Lacking GDNF", *Nature*, 1996, 382, 76–79.

Bar et al., "Glial–Derived Neurothrophic Factor in Human Adult and Fetal Intestine and in Hirschsprung's Disease," *Gastroenterology*, 1997, 112(4), 1381–1385.

Affolter et al., "Multiple requirements for the receptor serine/threonine kinase thick veins reveal novel functions of TGF–beta homologs during *Drosophila embryogenesis*", *Development*, 1994, 120, 3105–3117.

Arenas et al., "GDNF prevents degeneration and promotes the phenotype of brain noradrenergic neurons in vivo", *Neuron*, 1995, 15, 1465–1473.

Baloh et al., "TrnR2, a novel receptor that mediated neurturin and GDNF signaling through ret", *Neuron*, 1997, 18, 793–802.

Buj–Bello et al., "GDNF is an age–specific survival factor for sensory and automatic neurons", *Neuron*, 1995, 15, 821–828.

Davies et al., "Sulphated proteoglycan is required for collecting duct growth and branching but not nephron formation during kidney development", *Development*, 1995, 121, 1507–1517.

Dudley et al., "A requirement for bone morphogenetic protein–7 during development of the mammalian kidney and eye", *Genes Devel.*, 1995, 9, 2795–2807.

Durbec et al., "GDNF signalling through the Ret receptor tyrosine kinase", *Nature (London)*, 1996, 381, 789–793.

Ebendal et al., "Glial cell line–derived neurotrophic factor stimulates fiber formation and survival in cultured neurons from peripheral autonomic ganglia", *J. Neurosci. Res.*, 1995, 40, 276–284.

Ekbolm et al., "Induction of brush border antigens of the proximal tubule in the developing kidney", *Devel. Biol.*, 1980, 74, 263–274.

Ekbolm et al., "Transferrin as a fetal growth factor: acquisition of responsiveness related to embryonic induction", *Proc. Natl. Acad. Sci. (USA)*, 1983, 80, 2651–2655.

Grobstein, "Inductive epithelio–mesenchymal interaction in cultured organ rudiments of the mouse", *Science*, 1953, 118, 52–55.

Grobstein, "Inductive interaction in the development of the mouse metanephros", *J. Exp. Zool.*, 1955, 130, 319–339.

Hellmich et al., "Embryonic expression of glial cell–line derived neurotrophic factor (GDNF) suggests multiple developmental roles in neural differentiation and epithelial–mesenchymal interactions", *Mech. Devel.*, 1996, 54, 95–105.

Henderson et al., "GDNF: a potent survival factor for motorneurons present in peripheral nerve and muscle", *Science*, 1994, 266, 1062–1064.

Jing et al., "GDNF–induced activation of the Ret protein tyrosine kinase is mediated by GDNFR–a, a novel receptor for GDNF", *Cell*, 1996, 85, 9–20.

Kispert et al., "Proteoglycans are required for maintenance of Wnt–11 expression in the ureter tips", *Development*, 1996, 122, 3627–3637.

Kotzbauer et al., "Neuturin, a relative of glial–cell–line–derived neurotrophic factor", *Nature (London)*, 1996, 384, 467–470.

Kreidberg et al., "WT–1 is required for early kidney development", *Cell*, 1993, 74, 679–691.

Lin et al., "GDNF: a glial cell line–derived neurotrophic factor for midbrain dopaminergic neurons", *Science*, 1993, 260, 1130–1132.

Liu et al., "Comparative role of phosphotyrosine kinase domains of c–ros and c–ret protooncogenes in metanephric development with respect to growth factors and matrix morphogens", *Devel. Biol.*, 1996, 178, 133–148.

Luo et al., "BMP–7 is an inducer of nephrogenesis, and is also required for eye development and skeletal patterning", *Genes Devel.*, 1995, 9, 2808–2820.

Miller et al., "Signal transduction through β–catenin and specification of cell fate during embryogenesis", *Genes Devel.*, 1996, 10, 2527–2539.

(List continued on next page.)

*Primary Examiner*—Nancy Degen
*Attorney, Agent, or Firm*—Woodcock Washburn Kurtz Mackiewicz & Norris, LLP

[57] ABSTRACT

The effect of GDNF on kidney morphogenesis is disclosed. Methods for stimulating budding and branching of the ureteric epithelium, for stimulating axonal outgrowth, for maintaining ureteric epithelial cells in culture, for preventing apoptosis of ureteric epithelial cells, and for treating diseases using GDNF are also disclosed.

26 Claims, 7 Drawing Sheets

OTHER PUBLICATIONS

Montesano et al., "Identification of a fibroblast–derived epithelial morphogen as hepatocyte growth factor", *Cell,* 1991, 67, 901–908.

Montesano et al., "Induction of epithelial tubular morphogenesis in vitro by fibroblast–derived soluble factors", *Cell,* 1991, 66, 697–711.

Olive et al., "The F3 neuronal glycosylphosphatidylinositol–linked molecule is localized to gylcolipid–enriched membrane subdomains and interacts with L1 and fyn kinase in mouse cerebellum", *J. Neurochem.,* 1995, 65, 2307–2317.

Oppenheim et al., "Developing motor neurons rescued from programmed and axotomy–induced cell death by GDNF", *Nature (London),* 1995, 373, 344–346.

Pachnis et al., "Expression of the cRet protooncogene during mouse embryogenesis", *Development,* 1993, 119, 1005–1017.

Partanen et al., "Localization and quantitation of $125_I$ epidermal growth factor binding in mouse embryonic tooth and other embryonic tissues at different developmental stages", *Devel. Biol.,* 1987, 120, 186–197.

Perantoni et al., "Basic fibroblast growth factor can mediate the early inductive events in renal development", *Proc. Natl. Acad. Sci. (USA),* 1995, 92, 4696–4700.

Pichel et al., "Defects in enteric innervation and kidney development in mice lacking GDNF", *Nature (London),* 1996, 382, 73–76.

Rathjen et al., "Immunocytological and biochemical characterization of a new neuronal cell surface component (L1 antigen) which is involved in cell adhesion", *EMBO J.,* 1984, 3, 1–10.

Reichman–Fried et al., "Breathless, a Drosophila FGF receptor homolog, is required for the onset of tracheal cell migration and tracheole formation", *Mech. Devel.,* 1995, 52, 265–273.

Richter et al., "Influence of oxygen and culture media on plating efficiency of some mammalian tissue cells", *J. Natl. Cancer Inst.,* 1972, 49, 1705–1712.

Ritvos et al., "Activin disrupts epithelial branching morphogenesis in developing glandular organs of the mouse", *Mech. Devel.,* 1995, 50, 229–245.

Sainio et al., "Differential regulation of two sets of mesonephric tubules by WT–1", *Development,* 1997, 124, 1293–1299.

Sainio et al., "Neuronal characteristics in embryonic renal stroma", *Int. J. Dev. Biol.,* 1994, 38, 77–84.

Sánchez et al., "Renal agenesis and the absence of enteric neurons in mice lacking GDNF", *Nature (London),* 1996, 382, 70–73.

Santoro et al., "An epidermal growth factor receptor/ret chimera generates mitogenic and transforming signals: evidence for a ret–specific signaling pathway", *Molec. Cell. Biol.,* 1994, 14, 663–675.

Santos et al., "Involvement of hepatocyte growth factor in kidney develoment", *Devel. Biol.,* 1994, 163, 525–529.

Sariola et al., "Early innervation of the metanephric kidney", *Development,* 1988, 104, 589–599.

Saxén, "Organogenesis of the kidney", Cambridge University Press, Cambridge, 1987.

Saxén et al., "Embryonic kidney in organ culture", *Differentiation,* 1987, 36, 2–11.

Schmidt et al., "Scatter factor/hepatocyte growth factor is essential for liver development", *Nature (London),* 1995, 373, 699–702.

Schuchardt et al., "Renal agenesis and hypodysplasia in ret–k– mutant mice result from defects in ureteric bud development", *Development,* 1996, 122, 1919–1929.

Schuchardt et al., "Defects in the kidney and enteric nervous system of mice lacking the tyrosinc kinase receptor Ret.", *Nature (London),* 1994, 367, 380–383.

Schull et al., "Targeted disruption of the mouse transforming growth factor–beta 1 gene results in multifocal inflammatory disease", *Nature (London),* 1992, 359, 693–699.

Stark et al., "Epithelial transformation of metanephric mesenchyme in the developing kidney regulated by Wnt–4", *Nature (London),* 1994, 372, 679–683.

Suvanto et al., "Localization of glial cell line–derived neurotrophic factor (GDNF) and mRNA in embryonic rat by in situ hybridization", *Eur. J. Neurosci.,* 1995, 8, 816–822.

Suvanto et al., "Cloning, mRNA distribution and chromosomal localization of the gene for glial cell line–derived neurotrophic factor receptor beta, a homologue to GDNFR–alpha", *Hum. Mol. Gen.,* 1997, 6(8), 1267–1273.

Takahaski et al., "Ret transforming gene encodes a fusion protein homologous to tyrosine kinase", *Mol. Cell Biol.,* 1988, 7, 1378–1385.

Takeichi, "Cadherins in cancer: implications for invasion and metastasis", *Curr. Opin. Cell Biol.,* 1993, 5, 806–811.

Tomac et al., "Protection and repair of the nigrostriatal dopaminergic system by GDNF in vivo", *Nature (London),* 1995, 373, 335–339.

Torres et al., "Pax–2 controls multiple steps of urogenital development", *Development,* 1995, 121, 4057–4065.

Treanor et al., "Characterization of a multicomponent receptor for GDNF", *Nature (London),* 1996, 382, 80–83.

Trupp et al., "Functional receptor for GDNF encoded by the cRet proto–oncogene", *Nature (London),* 1996, 381, 785–789.

Uemura et al., "Zygotic Drosophila E–cadherin expression is required for processes of dynamic epithelial cell rearrangement in the Drosophila embryo", *Genes Devel.,* 1996, 10, 659–671.

Vainio et al., "Identification of BMP–4 as a signal mediating secondary induction between epithelial and mesenchymal tissues during early tooth development", *Cell,* 1993, 75, 45–58.

Vega et al., "Glial cell line–derived neurotrophic factor activates the receptor tyrosine kinase ret and promotes kidney morphogenesis", *Proc. Natl. Acad. Sci. (USA),* 1996, 93, 10657–10661.

Virtanen et al., "Diagnostic applications of monoclonal antibodies to intermediate filaments", *Ann. N.Y. Acad. Sci.,* 1985, 455, 635–648.

Vukicevic et al., "Induction of nephrogenic mesenchyme by osteogenic protein 1 (bone morphogenetic protein 7)", *Proc. Natl. Acad. Sci. (USA),* 1996, 9021–9026.

Wilkinson et al., "In situ hybridization and the three–dimensional reconstruction of serial sections", In: *Postimplantation Mammalian Embryos. A Practical Approach.,* A. Copp and D. Cockroft (eds.), Oxford University Press: London, 1990, 155–171.

Woolf et al., "Roles of hepatocyte growth factor/scatter factor and the met receptor in the early development of the metanephros", *J. Cell Biol.,* 1995, 128, 171–184.

Worby et al., "Glial cell line–derived neurotrophic factor signals through the RET receptor and activates mitogen–activated protein kinase", *J. Biol. Chem.,* 1996, 271, 23619–23622.

Wright et al., "Focal expression of glial cell line–derived neurotrophic factor in developing mouse limb bud", *Cell Tissue Res.,* 1996, 286, 209–217.

Wille et al., "Effects of Growth Factors, Hormones, Bacterial Lipopolysaccharides and Lipotechoic Acids on the Clonal Growth of Normal Ureteral Epithelial Cells in Serum Free Media" J. Cell. Physiol. 150:52–58, 1992.

Fortuna et al., "Critical Analysis of the Operative Treatment of Hirschsprung Disease." Arch. Surgery. 131(5) 520–524, Abstract Only, May 1996.

Hedlund et al. Posterior Sagittal Resection for Rectal Aganglionosis: Preliminary Results of a New Approach . . . J. Ped. Surgery 32(12) 1717–1720 Abstract Only, Dec. 1997.

Agarwala et al "Long Term Follow Up of Hirschsprung's Disease Review of Early & Late Complications." Indian Pediatrics 33(5) 382–386 Abstract only, May 1996.

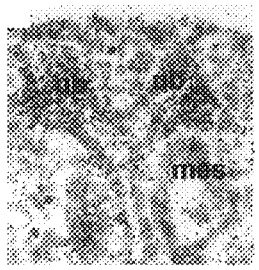 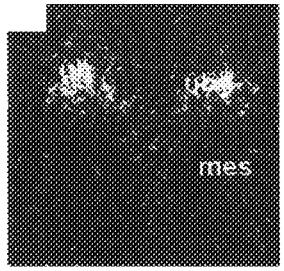 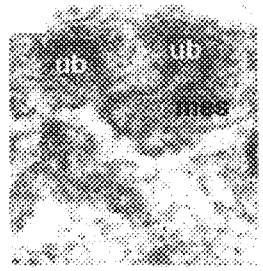 
FIG.1A    FIG.1B    FIG.1C    FIG.1D
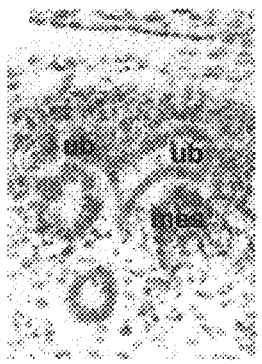 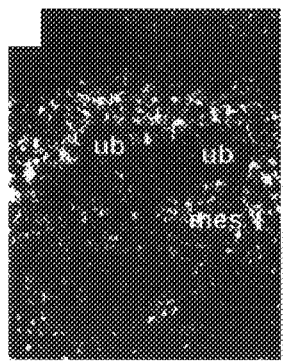 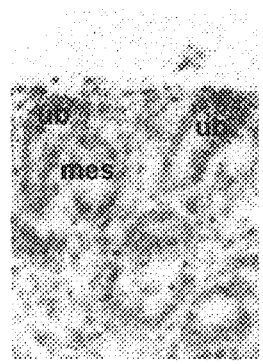 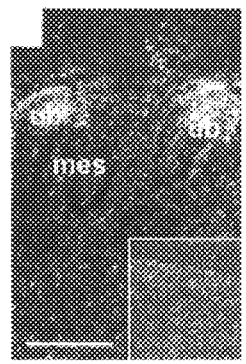
FIG.1E    FIG.1F    FIG.1G    FIG.1H

GLIAL CELL LINE-DERIVED NEUROTROPHIC FACTOR REGULATION OF URETERIC BUDDING AND GROWTH

Pursuant to 35 U.S.C. § 119(e), the present application claims priority benefit of application Ser. No. 60/021,964, filed Jun. 27, 1996, hereby incorporated by reference in its entirety.

FIELD OF THE INVENTION

The present invention relates to the effect of Glial cell-line derived neurotrophic factor ("GDNF") on cell differentiation and growth, in particular, on the growth and differentiation of ureteric epithelial cells and neurons.

BACKGROUND OF THE INVENTION

The shapes of different organs can be explained largely by two fundamental characteristics of their epithelial rudiments—the pattern of branching and the rate of proliferation. Glial cell line-derived neurotrophic factor his recently been implicated in the development of metanephric ureteric epithelium (Pichel, J. G., Shen, L., Sheng, H. Z., Granholm, A. -C., Drago, J., Grinberg, A., Lee, E. J., Huang, S. P., Saarma, M., Hoffer, B. J. Sariola, H. and Westphal, H. (1996). Nature (London) 382, 73–76; Sanchez, M. P., Silo-Santiago, I., Frisen, J., He, B., Lira, S. A. and Barbacid, M. (1996). Nature (London) 382, 70–73; Vega, Q. C., Worby, C. A., Lehner, M. S., Dixon, J. E. and Dressler, G. R (1996). Proc. Natl. Acad. Sci. (USA)93, 10657–10661).

Development of the ureter and urinary collecting duct system of the metanephric kidney is first triggered by a signal from the nephrogenic mesenchyme. This signal induces the nearby Wolffian duct to produce an outgrowth, the ureteric bud, which then elongates, invades the mesenchyme, and undergoes dichotomous divisions. Its tips induce condensation and epithelial conversion of the mesenchyme into excretory tubules (reviewed by Saxen, 1987). Kidney tubule induction and ureteric morphogenesis are regulated reciprocally (Grobstein, 1953; 1955). Attempts to identify the signals involved have traditionally concentrated on the induction of epithelial differentiation of kidney tubules, and some interesting candidate molecules have been identified (Kreidberg et al., 1993; Stark et al., 1994; Dudley et al., 1995, Luo et al., 1995; Perantoni et al. 1995; Torres et al., 1995; Vukieevic et al., 1996). Less is known about the control of ureteric bud growth and differentiation, although some growth factors, such as hepatocyte growth factor/scatter factor (HGF) (Santos et al., 1994; Woolf et al., 1995), transforming growth factor-$\beta$1 (TGF$\beta$1) (Rilvos et al., 1995), and extracellular matrix molecules (Davis et al., 1995) have been implicated in the regulation of its growth and branching. Moreover, HGF has been shown to regulate branching morphogenesis of kidney-derived Madin-Darby canine kidney (MDCK) epithelial cells in collagen-matrix cultures (Montesano et al., 1991a).

Recent data have shown that glial cell line-derived neurotrophic factor (GDNF) is expressed in the condensing mesenchyme that surrounds the developing ureteric system of kidneys (Hellmich et al., 1996; Suvanto et al., 1996). GDNF is a distant member of the TGF$\beta$ superfamily (Lin et al., 1993) and maintains dopaminergic, noradrenergic and motor neurones of the central nervous system (Lin et al., 1993; Tomac et al., 1995; Arenas et al., 1995; Henderson et al., 1994; Oppenheim et al., 1995; Yan et al., 1995) as well as various sub-populations of the peripheral sensory and sympathetic neurones (Henderson et al., 1994; Buj-Bello et al., 1995; Ebendal et al., 1995; Trupp et al., 1995).

One known receptor for GDNF is the cRet receptor tyrosine kinase (Takahashi et al., 1988; Trupp et al., 1996; Durbec et al., 1996), which is expressed in several tissues adjacent to sites of GDNF synthesis and it is autophosphorylated upon GDNF binding. The functional receptor complex of GDNF and cRet additionally includes novel type of glycosylphosphatidylinositol-lined (GPI) cell surface receptors, GDNFR-$\alpha$ (Jing et al., 1996; Treanor et al., 1996) or GDNFR-$\beta$ (Suvanto et al., 1997; also named TGF-$\beta$-related neurotrophic factor receptor, TmR2; Baloh et al., 1997). Comparative analysis of GDNFR-$\alpha$, GDNFR-$\beta$ and cRet expression suggests that multiple receptor complexes exist in vivo (Baloh et al. 1997, Suvanto et al. 1997). The ligand specificities of GDNFR-$\alpha$ and GDNFR-$\beta$ have not yet been fully resolved, but they bind both GDNF and its novel homologue neurturin (Kotzbauer et al. 1996), and both these GPI-linked receptors can mediate growth factor signaling via cRet (Baloh et al., 1997).

Transgenic mice deficient for GDNF, and those deficient for cRet, show remarkably similar phenotypes that are characterized by a severe defect in intestinal innervation, and renal aplasia or hypodysplasia (Pichel et al., 1996; Schuchardt et al., 1994; 1996). This observation, together with those from antibody inhibition experiments (Vega et al., 1996), suggests strongly that GDNF and cRet play a major role in development of renal epithelia. We disclose herein the target cell types and developmental functions of GDNF in kidney morphogenesis.

SUMMARY OF THE INVENTION

In one aspect, the present invention relates to a method for maintaining ureteric cells in culture.

In another aspect, the present invention relates to a method for preventing apoptosis of ureteric cells.

In still another aspect, the present invention relates to a method for stimulating ureteric budding of the Wolffian duct.

In yet another aspect, the present invention relates to a method for stimulating ureteric branching.

In a further aspect, the present invention relates to a method for treating Hirschsprung disease and renal dysplasia.

In yet a further aspect, the present invention relates to a method for stimulating axonal outgrowth of neuronal cells.

In still a further aspect, the present invention relates to a method for stimulating adhesion between ureteric cells.

In a still further aspect, the present invention relates to a method for stimulating the formation of basal lamina on ureteric cells.

BRIEF DESCRIPTION OF THE DRAWINGS

FIGS. 1A–H. cRNA in situ hybridization of GDNF and GDNF receptor mRNAs and GDNF binding to the $E_r17$ metanephric kidney. A. cRet transcripts are seen only in the tips of the branches of the ureteric tree but not in the mesenchyme. B. Corresponding dark field image. C. GDNFR-$\alpha$ mRNA is expressed by both the ureteric epithelium and metanephric mesenchyme. D. Corresponding dark field image. E. GDNF cRNA is expressed by the pretubular mesenchyme. F. Corresponding dark field image. G. $^{125}$I-GDNF binds to the tips of ureteric epithelium, but neither to the other segments of the ureter nor medullary structures. H. Corresponding dark field image. Insert: 250-fold excess of unlabeled GDNF competes out the $^{125}$I-GDNF-binding. mes-condensing metanephrogenic mesenchyme, ub=tip of the ureteric epithelium bar 200 $\mu$m, insert 40 $\mu$m.

DETAILED DESCRIPTION

Figure 2A:
FIGS. 2A–H. The effect of GDNF on branching of the ureteric epithelium in metanephric kidney and urogenital explants. Cell-type markers: cytokeratin-8 (branches of the ureter bud and Wolffian duct) and brush border epitopes (secretory nephrons) (A. and B.), rhodamine-conjugated DB-lectin (branches of the ureter bud and Wolffian duct, C.-F.) and L1 neural cell adhesion molecule (branches of the ureter bud, Wolffian duct and neuronal cells, G.) and cytokeratin-18 (branches of the ureter bud and Wolffian duct, H.). A. A metanephric kidney from $E_r13$ cultured with BSA-soaked bead with a normal branch pattern after two days in culture. B. Distortion of branching around a GDNF-soaked bead in a corresponding kidney explant. The nearby branches are distorted and show irregular branches pattern. C. Induction of a new bud (arrow) from the Wolffian duct in the caudal mesonephric area. D. Induction of a heterologous, abnormally broad bud from the cranial mesonephric area by a GDNF-soaked bead in an $E_r13$ urogenital explant after two days in culture. E. Failure to induce supernumerary buds by a HGF-soaked and F. TGFβ1-soaked bead from the $E_r13$ Wolffian duct. G. GDNF-soaked beads induce no supernumerary buds from the Wolffian ducts in the mice deficient for cRet. H. Corresponding wild type mouse explant showing supernumerary buds form the Wolffian duct (arrow), similar to those seen in rat. Note that also the nearest branches from the ureteric epithelium (*) are directed towards the bead. Ub=tip of the ureteric epithelium, Wd=Wolffian duct. Beads are surrounded with dashed line. Bar: A. and B. 100 μm, C., D., E. and F. 200 μm, G. and H. 80 μm.
Figure 2B:
Figure 2C:
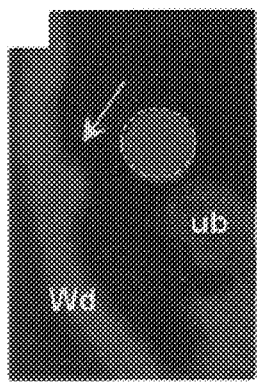

We have analyzed the target cell types and the mode of action of GDNF in the metanephric kidney. As disclosed herein, GDNF can induce ureteric bud formation from the Wolffian duct not only in the metanephric area, but also from the Wolffian duct segments outside the metanephric zone. The promotion of epithelial budding and branching morphogenesis requires cRet, and it does not take place in kidney cultures from cRet-deficient mice by GDNF-beads. As also disclosed herein, GDNF is a mesenchyme-derived signal that acts in a dosage-dependent manner on the epithelial target tissue. Further, the primary response to GDNF is not mitogenic and, in the hanging drop culture, it is characterized by decreased apoptosis, increased adhesiveness, secretion of basal lamina and maintenance of the polarization of the ureteric cells.

Although the maintenance and cell adhesion responses are directly mediated by GDNF, the branching response to GDNF is completely dependent on unknown mesenchyme-derived effector(s), possibly on mesenchyme-derived extracellular matrix molecules or growth factors. These growth-promoting signals are also provided to some extent by lung mesenchyme, but not the other mesenchymes tested. The tissue recombination data show further that the ureteric branching can be triggered by TGFβ1 and HGF, which implies redundancy in the regulation of ureteric differentiation. However, unlike GDNF, these growth factors do not direct the growth of the branches and do not promote budding from Wolffian ducts.

Thus, GDNF promotes ureteric morphogenesis by priming the Wolffian duct for bud initiation, perhaps by increasing cell adhesion in the target tissue and inducing wnt-11 expression. Besides GDNF and cRet, wnt-11 is also required for ureteric branching morphogenesis (Kispert et al., 1996). Thereafter, bud elongation may be promoted by other mesenchyme-derived effectors that may include HGF, TGFβ1 and extracellular matrix molecules.

In developing kidneys, GDNF is expressed exclusively by the pretubular metanephric mesenchyme. It becomes bound to its target tissue, the tips of the ureteric epithelium, where the branches of the collecting ducts are continuously being formed. Although one of its receptors, the GPI-linked protein GDNFR-α (Jung et al, 1996; Treanor et al., 1996), is expressed in both metanephric mesenchyme and ureteric bud, we could only verify GDNF binding to the tips of the ureteric branches where the cRet receptor tyrosine kinase is expressed. Furthermore, metanephric kidneys of mice deficient for cRet (Schuchardt et al., 1994, 1996) did not respond to GDNF. These data show that the ureteric epithelium is the main target cell type of GDNF in the embryonic kidney.

Previous studies with GDNF-deficient mice (Pichel et al, 1996; Treanor et al. 1996) and with neutralizing antibodies to GDNF (Vega et al, 1996) have shown that GDNF is necessary for development of the ureteric bud. In our experiments supernumerary budding from the Wolffian duct was induced by GDNF-soaked agarose beads, initially suggesting that GDNF could act as a mitogen upon the epithelial cells. However, isolated ureteric buds did not respond to GDNF by increasing cell proliferation, but by maintaining their epithelial morphology, showing increased adhesiveness, and extracellular matrix synthesis. This observation is consistent with the data of Liu et al. 1996, who showed that cRet modulates extracellular matrix synthesis by ureteric cells. Still, the mechanism and mediators of the increased cell adhesion remain to be elucidated. They may include wnt-11, a member of the wnt family of signal transducing molecules that could be up-regulated by GDNF in the Wolffian duct. Interestingly, wnts regulate cell adhesion and signal transduction through cadherins and catenins (reviewed by Miller and Moon, 1996) and cRet has a cadherin-like domain in its extracellular part (reviewed by Takeichi, 1993) that might be involved in the cell adhesion/signal transduction response.

Thus far the only mesenchymes that have been shown to support ureteric growth and branching are metanephrogenic and lung mesenchymes (Grobstein, 1955; Saxén, 1987. Kispert et al, 1996). As disclosed herein, we have recombined various heterologous mesenchymes with isolated early ureteric buds and added GDNF. None of the mesenchymes tested supported the development of early ureteric buds without exogenous GDNF. The lung mesenchymes supplemented by GDNF-containing medium or beads supported the branching of the early ureteric buds, showing that GDNF can promote branching when combined with a competent heterologous mesenchyme. It has been shown that lung mesenchyme induces ureteric branching and maintains wnt-11 expression of the tips of the ureteric bud (Kispert et al., 1996). We repeated these experiments and show that, in our culture system, the branching response is critically dependent on the stage of the bud. Only late, T-shaped buds undergo branching without exogenous GDNF.

Competence of heterologous mesenchymes to support the GDNF action turned out to be very restricted. Tooth, salivary, and limb mesenchymes did not support ureteric branching even with GDNF (although limb mesenchymes, for instance, show endogenous GDNF expression; Wright and Snider, 1996). Gut mesenchyme, a rich source of GDNF, did not support ureteric branching. These findings suggest that 1) either gut, salivary gland, tooth, and limb mesenchymes all lack a factor essential for ureteric branching or 2) they inhibit the GDNF response, for example, by competing out GDNF from the ureteric binding. The latter alternative is unlikely because GDNF tested up to the concentration of 50 ng/ml did not promote branching in the gut mesenchyme recombinations. The most plausible explanation is that the mesenchymes lack effectors, so far unidentified, for bud elongation. These molecules may not represent the GPI-linked GDNF receptors, because all mesenchymes tested in the recombination assays express either GDNFRα or GDNFRβ (Treanor et al. 1996, Baloh et al. 1997, Suvanto et al. 1997). Our data underline further the necessity for many simultaneously-acting effectors to promote normal branching morphogenesis.

In ureteric bud-lung mesenchyme recombination cultures, the branching response of ureter bud was promoted not only by GDNF, but also by TGFβ1 or HGF. However, unlike mice lacking GDNF (Pichel et al., 1996; Sanchez et al., 1996), mutant mice lacking TGF-β1 or HGF (Shull et al, 1992; Schmidt et al., 1995) show no apparent defects in kidney morphogenesis, suggesting that these molecules are not necessary for, or redundant in, kidney development in vivo. Tissue culture studies (Ritvos et al, 1995; Woolf et al, 1995), antibody inhibition experiments (Woolf et al, 1995) and studies with desulphated kidneys (Davies et al, 1995) have indicated roles for these growth factors in regulation of ureteric growth. Our data suggest that they act later than GDNF because, unlike GDNF, they did not initiate buds from the Wolffian duct inside or outside the normal nephrogenic area.

Sulphated glycosaminoglycans ("GAGs") of the extracellular matrix are important to ureteric bud growth and branching. The ureteric buds of kidneys deprived of sulphated GAGs show neither growth nor branching. HGF has been reported to elongate ureteric epithelium in desulphated kidneys (Davies et al, 1995) and antibodies to HGF inhibit kidney morphogenesis in organ culture (Woolf et al, 1995). We therefore tested the ability of GDNF and HGF to restore ureteric morphogenesis to kidney rudiments deprived of sulphated GAGs, but new branches grew only very little. Because HGF did not significantly elongate the branches when added together with GDNF, unidentified growth-promoting molecules may act between GDNF and HGF response.

We could not induce branching of the isolated ureteric buds, deprived of mesenchymal support in hanging drop or collagen gel cultures, with GDNF, HGF or TGFβ1. This further suggests that additional growth factors or sulphated GAGs from the mesenchymal cells are needed to complete ureteric morphogenesis. Sulphated GAGs in the extracellular matrix may be needed for GDNF synthesis or to attach GDNF to the matrix, since in desulphated kidneys GDNF protein levels were down regulated, although the mesenchyme is induced and differentiates (Davies et al, 1995).

Activation of the cRet receptor tyrosine kinase is mitogenic for some cells (Santoro et al, 1994). In neuroblastoma cells lines, for example, cRet utilizes the MAP-kinase signaling pathway to activate cell proliferation (Worby et al. 1996). We evaluated the possible mitogenic effects of GDNF on ureteric epithelial cells growing without a supportive matrix or mesenchyme. In these hanging drop cultures GDNF was not mitogenic, but it did enhance survival, cell polarization and adhesion of the bud cells. Presumably, the mitogenic effects of GDNF in the kidney, described earlier by Vega et al. (1996), are indirect and due to other mesenchyme-derived effectors acting together with or downstream to GDNF.

There is an interesting precedent for branching processes that do not depend on cell proliferation. The tracheal network and Malpighian tubules of developing Drosophila embryos are epithelial structures that undergo tube formation and branching morphogenesis analogous to mammalian kidney morphogenesis. In these organs, bud formation and branching do not require cell proliferation by they are rather based on cell migration, elongation and cell adhesion. Drosophila E-cadherin has been associated to tracheal and Malpighian tubule formation (Eimeria et al., 1996). Drosophila fibroblast growth factor (DFGF) and its receptor breathless (Reichman-Fried and Shilo, 1995) as well as a TGFβ superfamily member decapentaplegic (Affolter et al., 1994), guide the migration of tracheal cells during branching morphogenesis. Our present data suggest that the central events taking place during the initiation of ureteric branching morphogenesis might be similar to those of Drosophila tracheal network and Malpighian tubule initiation.

Several GPI-anchored proteins are know to mediate signals for cell adhesion. Since the GDNF binding data did not reveal GDNFR-α or GDNFR-β as major GDNF binding proteins in the kidney, they might have other functions unrelated to growth factor binding. One GPI-linked protein, F3, interacts in mouse cerebellum with neural cell adhesion molecule L1 (Olive et al., 1995), a molecule that is also expressed on the ureteric epithelium (Sainio et al., 1994). GNDFR-α or GDNFR-β might have similar functions. These results do not contradict the suggested interplay model between cRet and GNDFR-α (Jing et al. 1996; Treanor et al., 1996) or GDNFR-β (Baloh et al., 1997; Suvanto et al., 1997) in GDNF signalling.

Although GDNF did not act primarily as a mitogen on isolated bud cells, the ureteric epithelial cells were mostly directed towards the beads in explant cultures. GDNF seems to determine the direction of growth from the target epithelia. This response may be mediated by a GDNF gradient from the pretubular mesenchyme acting most efficiently on the nearby epithelial cells. This would require a clear dosage-dependent mode of action of GDNF. We could verify it in both tissue recombination and urogenital block cultures, in which all other conditions, except the concentration of GDNF, remained the same. In urogenital block cultures the directed growth was observed not only in the metanephric region but also in the more cranial segments of the Wolffian duct. These data suggest that, if other mesenchyme-derived factors determine the orientation of buds, they should be general and permissive in nature, such as mitogenic growth factors in extracellular matrix molecules.

In summary, GDNF fulfils the criteria to be an important kidney inducer that acts early in the initiation of ureteric bud development. The growth factor shows expression and binding patterns compatible with its apparent role in the kidney, and it has a clearly defined function in the ureteric morphogenesis. HGF and TGFβ1 show, in part, similar biological effects on ureteric epithelium, but they lack some specific characteristics of GDNF. They neither induce bud formation from the Wolffian duct nor promote the basal lamina synthesis by the ureteric bud. These differences suggest that they act downstream to GDNF and represent the expanding set of mesenchyme-derived growth factors with overlapping, partially redundant developmental functions.

Agarose beads soaked in GDNF also had an effect upon axonal outgrowth by neuroblasts in embryonic explants from wild-type embryos. A large number of axons were observed growing towards and, eventually, encapsulating the GDNF-soaked beads. Similar results were not observed in explants ret.k homozygous embryos, suggesting that the lack of response is exclusively due to the absence of c-ret receptor tyrosine kinase, and that normal c-ret functioning is necessary for GDNF signaling in the peripheral nervous system.

The foregoing indicates that, not only is GDNF essential for kidney morphogenesis, but also for the development of the peripheral nervous system. Additional studies, using GDNF knockout mice, confirm that GDNF is essential for ureteric budding and branching, as well as indicate that GDNF is essential for innervation of the gastrointestinal tract. Homozygous GDNF knockout mice were essentially devoid of enteric parasympathetic cholinergic ganglion cells.

Some human genetic disorders, i.e., Hirschsprung disease, are characterized by defects in gastrointestinal innervation. Mutations in the human ret locus have been demonstrated in some familial forms Hirschsprung disease. The loss of enteric neurons in GDNF knockout mice suggests that mutations in the GDNF gene may cause Hirschsprung disease. Certain renal dysplasias might also be linked GDNF gene defects. The GDNF locus may be implicated in human disorders in which target fields of GDNF are affected, such as Parkinson's disease and Alzheimer's disease. GDNF was shown to promote survival of adult substantia nigra neurons in vivo following pharmacological treatments and lesions that mimic Parkinsonian syndromes (Beck et al., 377 Nature 339, 1995; Tomac et al., 373 Nature 335, 1995, incorporated herein by reference). It is contemplated that GDNF will be useful in treating such genetic disorders, as well as other disorders. The actual dosage of GDNF administered may take into account the size and weight of the patient, whether the nature of the treatment is prophylactic or therapeutic in nature, the age, weight, health and sex of the patient, the route of administration, and other factors.

The GDNF can be administered in amounts effective to maintain the viability of renal and enteric neuronal cells. Such amounts may vary depending on the nature and extent of the disease, and other factors. Dosage determinations will depend upon the individual and can be determined by one skilled in the art. It is also contemplated that GDNF can be administered with pharmaceutically acceptable carriers such as are known in the art.

The term "contacting" as used herein includes, but is not limited to, immersion in a solution containing GDNF, application of GDNF in solution, and application of GDNF-coated beads.

The term "application" as used herein includes in vitro, in vivo, and in situ administration.

The term "about" as used herein means ± about 10%, preferably ± about 5%.

EXAMPLES

Unless otherwise specified, the following materials/procedures were utilized/followed.

Animals

Sprague-Dawley or Wistar rat embryos, of various stages of gestation, were used throughout the study. Rats were mated overnight and the next day was defined as embryonic day 0 ($E_r$0). The gestation stage was further estimated by the size of the limb buds and the stage of the kidney was verified visually under a stereo-microscope after dissection. In desulphation experiments, $E_m$11 mouse kidney rudiments were also used. Generation of the transgenic mice deficient for cRet has been described in Schuchardt et al. (1994, 1996).

Organ culture

Microdissection was used to isolate the following tissues; early mouse $E_m$ 11 bud-negative metanephric mesenchymes with adjacent Wolffian ducts, mouse $E_m$ 11 bud-stage kidney rudiments; rat $E_r$ 13 bud-and T-bud-stage metanephric kidneys; and $E_r$13 whole urogenital blocks (including metanephric kidney, Wolffian duct, genital ridge and mesonephros). These tissues were then cultured in Trowell-type dishes either intact or as separated nephrogenic mesenchymes and ureteric buds, separation being performed using 0.25% pancreatin-trypsin. Two types of culture media were used; a) MEM (Eagle's Minimum Essential Medium, Gibco) supplemented with 5–10% fetal bovine serum (FBS) (Bioclear), b) I-MEM (Improved Eagle's Minimum Essential Medium, Gibco), originally based on MEM modified by Richter et al. (1972) supplemented with 50 μg/ml iron-loaded transferrin instead of serum (Ekblom et al., 1983).

For the tissue recombinant cultures different mesenchymes (lung, salivary gland, limb, and gut) from $E_r13$ to $E_r14$ rats and tooth mesenchyme from $E_m11$ mouse were separated with pancreatin-trypsin from their respective epithelia, and cultured in recombination with isolated ureteric buds. Organs were cultured on Nuclepore filters (pore-size 1 μm or 0.1 μm; Costar) placed on top of a metal grid in a Trowell-type organ culture. Separated ureteric buds were also cultured in 30 μl drops of medium hanging from a lid of a Petri dish (Nunclon), the bottom of the dish being filled with sterile phosphate buffered saline (PBS). The microdissection and tissue culture techniques have been described in detail by Saxén and Lehtonen (1987), incorporated herein by reference.

Growth Factors

Human recombinant GDNF was provided by PeproTech Inc. and Promega. GDNF stock was dissolved in sterile PBS and 100 ng/μl; concentrations ranging from 1 ng/ml to 100 ng/ml were tested in tissue recombination and hanging drop cultures. TGFβ1, was provided by Dr. Marikki Laiho (University of Helsinki). It was dissolved to make a 50 ng/μl stock, and concentrations ranging from 1 pg/ml to 100 ng/ml were tested in cultures. Human recombinant HGF (Sigma or Collaborative Biomedical was kept as a 50 ng/μl stock, and concentrations from 1 ng/ml to 100 ng/ml were used in culture experiments. All growth factor stocks were stored at −70° C. until used. Culture medium was changed every second day.

Antibodies

Primary antibodies included polyclonal antibodies to EHS-tumor laminin (Gibco), monoclonal antibodies to cytokeratin-8 (Amersham), polyclonal antibodies to mouse L1 neural cell adhesion molecule (Rathjen and Schachner, 1984), and polyclonal antibodies to rat brush border epitopes (Ekblom et al., 1980). Secondary antibodies comprised rhodamine-conjugated goat-anti-mouse IgG and fluorescein-conjugated donkey-anti-rabbit IgG (Jackson Immuno-Research Lab.). $E_m11$ mouse kidneys were stained using the collecting-duct specific stain anti-calbindin-D-28K (Davies, 1994) or with monoclonal antibodies to cytokeratin-18 (Virtanen et al., 1985). In some experiments, ureteric epithelium was visualized by rhodamine-conjugated *Dolichos biflorus*-agglutinin (Vector) at 25 μg/ml. concentration.

Whole-mount staining

Organ rudiments, from embryos and cultures, were stained by the whole-mount immunocytochemical technique described by Sariola et al. (1988) with some modifications. Briefly, tissue explants were fixed in ice-cold methanol for 5 minutes, washed in PBS containing 11% sucrose and 1% bovine serum albumin (BSA), and incubated overnight in secondary antibodies, washed three times for two hours each in PBS, and mounted in Immumount (Shandon). All antibody incubations were done in Eppendorf tubes at +4° C. Hanging drop cultures were stained using a similar method but, immediately before fixation, they were attached to filters by either Matrigel (Becton Dickinson) or 2% agarose in MEM.

Growth factor-soaked agarose beads

For bead experiments, $E_r13$ rat kidneys, $E_r13$ urogenital blocks, and $E_m11$ mouse bud-positive and bud-negative metanephric rudiments were cultured as described above. Separated $E_r13$ rat kidneys, $E_r13$ urogenital blocks, and $E_m11$ mouse bud-positive and bud-negative metanephric rudiments were cultured as described above. Separated $E_r13$ kidney ureteric buds without metanephric mesenchyme were recombined with lung mesenchyme from the embryo.

To prepare growth factor-soaked beads, agarose beads (Affi-gel Blue; BioRad) of 80 to 120 mesh were washed extensively in sterile PBS, then incubated in 5 μl of growth factor solutions (100 ng/μl (GDNF), 50 ng/μl and 10 ng/μl (GDNF, HGF and TGFβ1)) or in control 1% BSA/PBS as described (Vainio et al., 1993). They were placed by a micro-capillary next to ureteric buds or Wolffian ducts of the embryos mentioned above, and also of $E_m11$ urogenital blocks (GDNF only) from transgenic mice deficient for cRet (Schuchardt et al., 1994). Tissues were cultured for three to five days with the beads and then processed by whole-mount immunohistochemistry.

Example 1

GDNF binds selectively to the tips of the ureteric bud epithelium

We compared the expression patterns of cRet, GDNFR-α, and GDNFR mRNAs by in situ hybridisation. Single-stranded antisense and sense cRNA probes were synthesised and labeled with $^{35}$S-UTP (Amersham) using appropriate RNA polymerases. Rat GDNFR-α probe was cloned forward (nucleotides 294–313) 5' GCG GCA CCA TGT TAG CC 3' [SEQ ID NO:1] and reverse (nucleotides 1020–1039) 5' CAG ACT CAG GCA GTT GGG CC 3' [SEQ ID NO:2]. The identity of the cloned fragment was verified by direct sequencing with a Pharmacia A.L.F. automatic DNA sequencer. The c-ret probe spanned the tyrosine kinase domain of mouse c-ret (nucleotides 2534–3217; Pachnis et al., 1993). The cloning of rat GDNF probe for in situ hybridisation has been described in Suvanto et al., 1996, incorporated herein by reference.

In situ hybridisation for sections was performed according to Wilkinson and Green (1990) with some modifications. Briefly, whole rat $E_r13$ to $E_r17$ embryos or dissected kidneys were fixed in fresh, neutral buffered paraformaldehyde (PFA) for 2 hours at room temperature or overnight at +4° C., rinsed in PBS and processed for paraffin sectioning at 7 μm on silanized slides. Slides were deparaffinised, treated with proteinase K (15–40 μg/ml, Sigma), post-fixed in 4% PFA, rinsed in PBS and hybridised overnight at +52° C. with cRNA probes. The sections were washed at high stringency conditions, treated with RNAse A (Boehringer Mannheim), dehydrated and air dried. For autoradiography the slides were dipped in Kodak NTB-2 emulsion, exposed for 12 days to 2 weeks, developed in D-19 (Kodak), counterstained in Harris hematoxylin (Shandon) and mounted in Mountex. Photos were taken with an Olympus AX70 Provis microscope. Hybridisation with probes in the sense orientation resulted in only low background labeling (data not shown).

For in situ binding assays, 1–2 μg recombinant human GDNF was treated with Chloramine T (Serva) for 30–40 seconds in the presence of 250 μCi of [$^{125}$I] Na (Amersham) and the reaction was stopped by $Na_2S_2O_5$ and NaI. Unbound Na [$^{125}$I] was separated by gel filtration with Sephadex G25 PD-10 Columns (Pharmacia). Specific Activity determined from trichloroacetic acid-precipitated aliquots of the reaction product, was approximately 100 μCi/mg. Kidneys from $E_r13$ to $E_r17$ rats were incubated at room temperature with 10 ng/ml of $^{125}$I-GDNF for 90 minutes in MEM with 120 mM Hepes (Gibco) and 0.1% BSA as described by Partanen and Thesleff (1987). Samples were washed at +4° C., first for 60 minutes in the binding medium, then four times for 30 minutes in PBS, and were fixed in fresh buffered 4% PFA embedded in paraffin, and serially sectioned at 7 μm. Binding of $^{125}$I-GDNF was competed with 250-fold excess of unlabeled GDNF, and kidneys were processed fro autoradiography as described for in situ hybridisation (see above).

The results are depicted in FIG. 1. cRet mRNA was located to the tips of the branches of the ureteric bud (FIGS. 1A, B; Pachnis et al., 1993), but was not expressed by the nephrogenic mesenchyme or by its derivatives as reported by Liu et al. (1996). The α-receptor (FIGS. 1C, D) showed an expression pattern that overlapped both GDNF (FIGS. 1E, F; see also Hellmich et al., 1996; Suvanto et al., 1996) and cRet, being expressed in condensing pretubular mesenchyme, in early secretory nephrons and in the tips of the ureteric epithelium.

$^{125}$I-GDNF bound selectively to the tips of the ureteric bud branches (FIGS. 1G, H), and the binding could be competed out completely by a 250-fold excess of unlabeled GDNF (FIG. 1H, insert). Very little binding was detected in the condensing nephrogenic mesenchyme and none in other regions of the kidney, for instance in subcapsular uniduced mesenchyme and smooth muscle layer ureteric pelvis, where GDNFR-β is expressed (see Suvanto et al., 1997).

Example 2

Figure 2D:
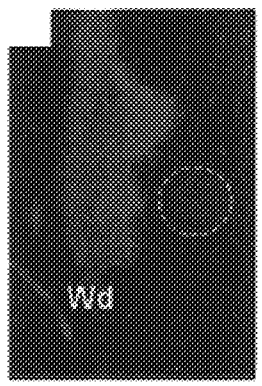
Figure 2E:
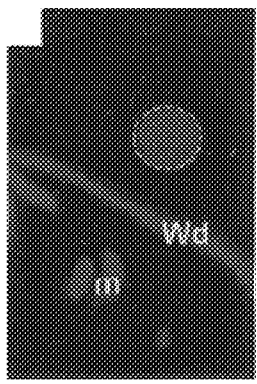
Figure 2F:
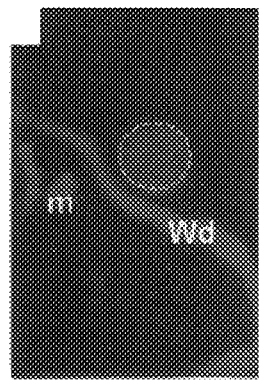
Figure 2G:
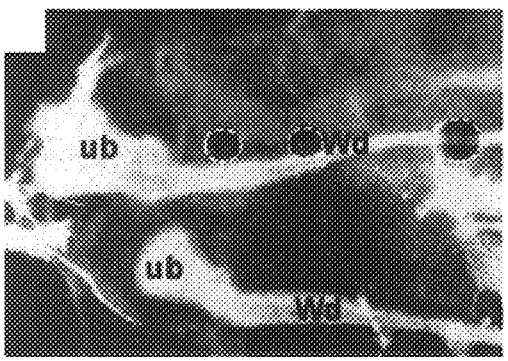
Figure 2H:
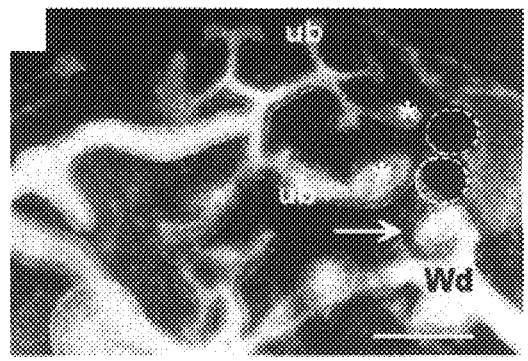

GDNF promotes ureteric budding from the Wolffian duct and affects ureteric branching Growth factor-soaked agarose beads were placed as follows; a) next to early $E_m11$ metanephric rudiments prior to ureteric budding from the Wolffian ducts; b) next to $E_m11$ and $E_r13$ kidney rudiments that had already formed a small ureteric bud from the Wolffian duct; c) next to corresponding whole urogenital explants. In embryonic rat kidneys already possessing a branching ureteric bud, the GDNF-beads, soaked in concentrations of 50 to 100 ng/μl or GDNF, distorted the branch pattern by expanding the diameter of the nearby branches (FIGS. 2A, B). They also induced the formation of supernumerary buds from the metanephric (precloacal) segments outside the metanephric field (the caudal mesonephric segment), where the Wolffian duct is not normally budding. (FIG. 2D; See Sainio et al., 1997 for the morphology of the Wolffian duct in mesonephros region). The average number of heterologous buds in the mesonephric segment was three (n=50). Most (85%) of the supernumerary buds were directed towards the GDNf-soaked beads. Only occasional, small supernumerary buds were induced by beads soaked in 10 ng/μl of GDNF. Beads soaked in 1% BSA (n=41), or 1, 10 or 100 ng/μl of TGFβ1 (n=15) or HGF (n=15) induced neither supernumerary budding from the Wolffian duct nor affected the number of branches in late embryonic kidneys (FIGS. 2E, F), but beads soaked above concentrations of 10 ng/μl of TGFβ1 and HGF did increase the length of the normal ureteric branches, as already described (data not shown; see Ritvos et al., 1995; Woolf et al., 1995; Davies et al., 1995). When urogenital blocks from mouse embryos deficient for cRet (Schuchardt et al., 1994) were cultured with GDNF-soaked beads, the Wolffian duct (FIGS. 2G, H), and the occasional ureteric buds present in these embryos showed no distortion of their branches by GDNF.

We also tested the effect of GDNF on isolated nephrogenic mesenchymes. Concentrations of 10 to 50 ng/ml of GDNF, in a chemically-defined or serum-supplemented culture media, neither induced epithelial differentiation nor any other morphological change.

Example 3

GDNF increases cell adhesion

Figure 3A:
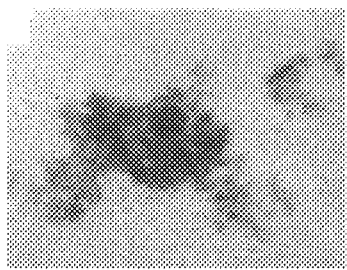
FIGS. 3A–J. The effect of GDNF on the epithelial morphology and adhesiveness of two ureteric buds growing in hanging drop culture (at 24 hours). Stereomicroscopic imagines (A., C., and E.), whole-mount immunohistochemisty for LI neural cell adhesion molecule (B., D. and F.) and electron microscopic analysis (G.-J.). Note that A. and B. depict only one unfused bud from the control culture, C. and D. two fusing buds growing with 50 ng/ml of GDNF, and E. and F. two fusing buds growing with 50 ng/ml HGF. A. Two ureteric buds without exogenous growth factors are shedding cells. B. L1 staining shows the disorganized pattern of a bud remnant without exogenous growth factors. C. and D. The two buds growing in GDNF or E. and F. in HGF maintain their epithelial, balloon-shaped morphology and regularly fuse in the hanging drop. G. Transmission electron microscopic analysis of ureteric buds growing without exogenous growth factors or, H., with 50 ng/ml of HFG shows tight junctions but no basal lamina. I. In 50 ng/ml of GDNF the bud is surrounded by a thin basal lamina (arrows), J., resembling lamina densa at the tip of a normal ureteric bud. ub=ureter bud. Bar A., C. and E. 200 μm B., D. and F. 400 μm, G.–J. 200 nm.
Figure 3B:
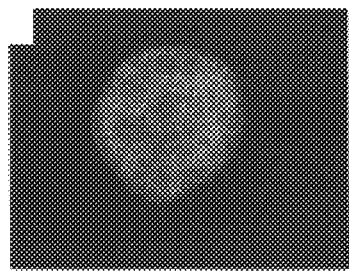
Figure 3C:
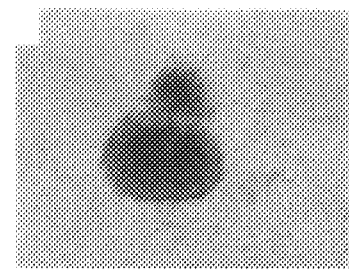
Figure 3D:
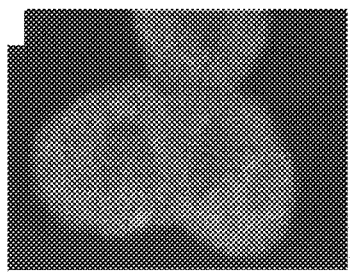
Figure 3E:
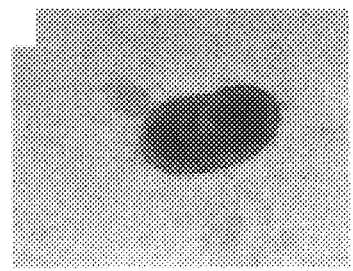
Figure 3F:
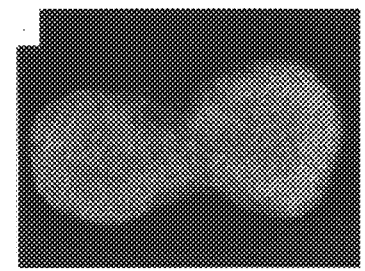

To determine the immediate effect of GDNF on ureteric epithelium, pairs of isolated ureteric buds were grown in hanging drop cultures with or without GDNF, HGF or TGFβ1. Under these conditions, i.e., without a supportive matrix, ureteric buds did not form branches in response to any of the growth factors. Control buds remained small and shed cells so that their epithelial morphology was disrupted (FIGS. 3A, B). However, in the presence of GDNF, the two buds in one hanging drops soon fused together, shed only a few cells, and retained their epithelial morphology (FIGS. 3C, D). The effect of HGF in hanging drops was similar to that of GDNF (FIGS. 3E, F). The percentage of scattered cells in the bud cultures was 60, 10 and 10% in control, GDNF and HGF cultures, respectively. TGFβ1 response was characterised by complete dissociation and extensive death of the cells, if TGFβ1 was applied at concentrations above of 1 ng/ml. Below that concentration, TGFβ1 did not have any effect on bud fusion, their morphology or scattering of cells.

Apoptosis of the ureteric epithelial cell in hanging drop cultures was analyzed by the ApopTag labeling kit (Oncor) based on the TUNEL technique (in situ terminal transferase end-labeling of fragmented DNA; Gacrieli et al., 1992) according to the manufacturer's instructions with some modifications. Ureteric buds, after 24 hours in hanging drop culture with or without GDNF, were placed on filters and immobilized with a drop of 2% agarose. Tissues were fixed as whole-mounts in 10% formalin, washed in PBS and post-fixed with 95% ethanol/5% acetic acid for 30 min. Thereafter the manufacturer's step-by-step protocol was followed. The samples were double-stained with fluorescein-conjugated goat anti-digoxigenin (Boehringer Mannheim) and monoclonal antibodies against cytokeratin-8, followed by rhodamine-conjugated anti-mouse IgG antibodies (Jackson Laboratories).

TUNEL-labeling of the ureteric buds in GDNF-or HGF-supplemented hanging drop cultures showed a decrease in the number of apoptotic cells as compared to buds growth in control medium or buds supplemented with TGFβ1.

Figure 3G:
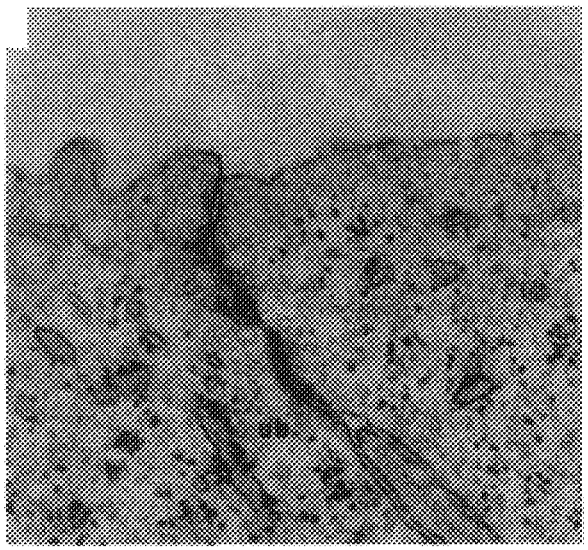
Figure 3H:
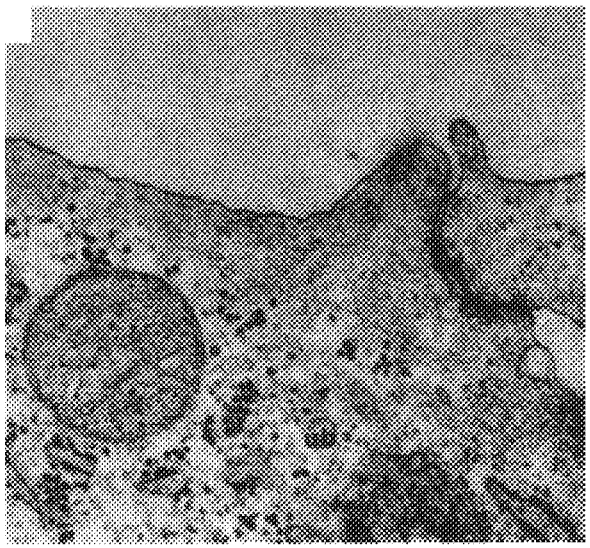
Figure 3I:
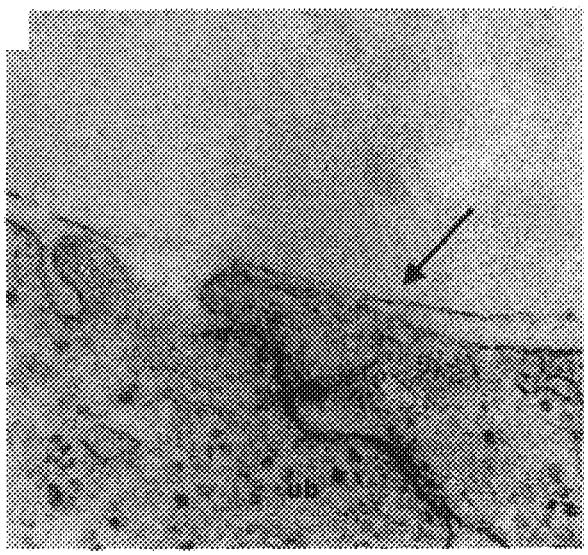
Figure 3J:
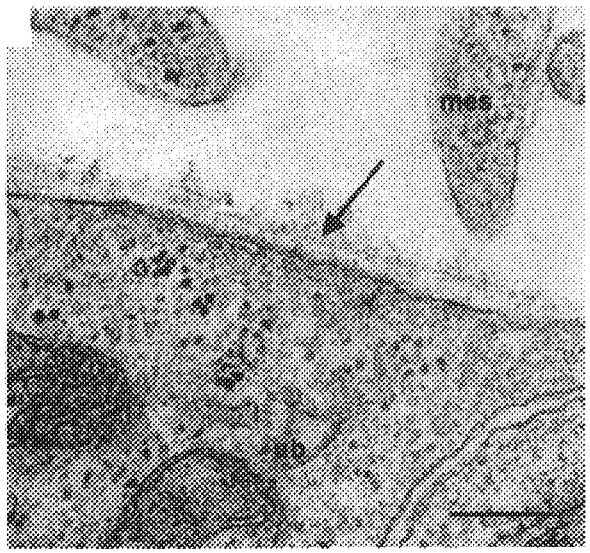

The morphology of separated buds grown in hanging drop cultures with or without GDNF or HGF was further analyzed by electron microscopy. For electron microscopy, isolated ureteric buds, grown 24 hours in hanging drop cultures and thereafter glued on Nuclepore filters with agarose, and freshly isolated, $E_r13$ kidneys were fixed in 2.5% glutaraldehyde in 0.1M phosphate buffer, pH 7.2. After ethanol dehydration, the samples were embedded in LX-112 resin (Ladd Research Industries, Inc.), sectioned and examined in a Jeol 1200 EX electron microscope. The results are depicted in FIGS. 3G–I. The buds, grown in control medium, showed only few tight junctions and no basal lamina (FIG. 3G). In the buds grown with HGF or GDNF, the cells showed well-developed tight junctions (FIGS. 3H, I). Further, with GDNF, a thin basal lamina (FIG. 3I), resembling the lamina densa of the basement membrane at the tip of the normal ureteric buds was present (FIG. 3J).

To monitor the effect of GDNF and HGF on cell proliferation, separated ureteric buds were cultured in hanging drops as described above, and 5-bromo-2'-deoxyuridine (BrdU) cell labeling reagent (Amersham) was used according to manufacturer's instructions. Briefly, two $E_r13$ ureteric buds in each 30 μl hanging drop were cultured for 24 or 48 hours with or without 50 ng/ml GDNF in either chemically-defined 1-MEM or MEM supplemented with 10% FBS. The medium in the drop was then changed to fresh medium containing the BrdU-label. Cultures were incubated at +37° C. for 30 minutes to one hour, after which they were fixed for whole-mount immunohistochemistry. Monoclonal antibodies to BrdU (Amersham) were used for doubleimmunofluorescence-labeling with polyclonal L1 neural cell adhesion molecules antibodies that served as an ureteric epithelial cell maker (Sainio et al., 1994). Because the isolated ureteric buds scatter cells in to the medium, the BrdU date reflect the mitotic index in the bud explants but not in the cells scattered in the cultured drop.

Figure 4:
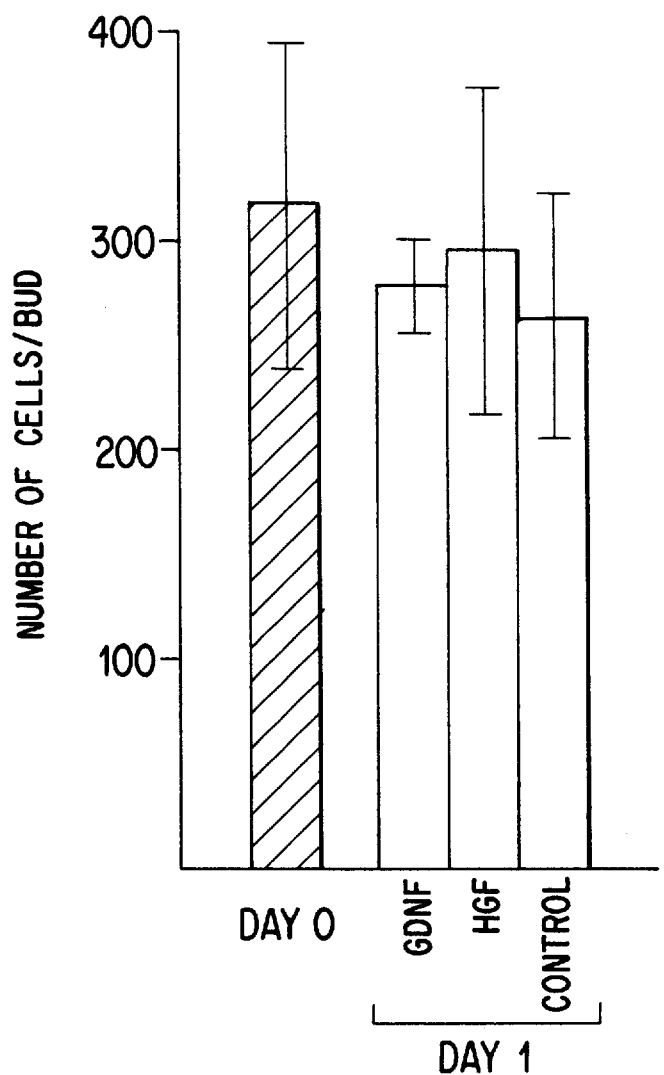
FIG. 4. The number of cells in a ureteric bud from $E_r13$ kidney (day 0, n=24) grown for 24 hours (day 1) with or without 50 ng/ml of GDNF or HGF (n=20 in each media). No difference is seen in the cell number in any media.

The BrdU data were verified further by counting both the enzymatically dissociated and scattered cells of separated ureteric buds either immediately after the dissection or after 24 hours in hanging drop cultures with or without ectopic growth factors (FIG. 4). Culture media with scattered cells from 10 drops containing two buds each were first pooled, collected to Eppendorf tubes and centrifuged. The scattered cells in 20 μl were then pipetted to silanised objective slides, air dried at +37° C. fixed with neutralised 10% formaldehyde, rinsed in PBS and Hoechst fluorochrome 33342, counterstained with Harris hematoxylin and mounted with Immumount. The buds in each drop were collected and dissociated with 1 ml pancreatin-trypsin and trypsin-EDTA at +37° C. for 20 minutes in separate Nunclon 3 cm culture dishes. The dissociated cells were collected in a small volume under a stereo microscope and placed on silanised objectives slides, and drops were air dried, fixed and stained as described above. Cells in each slide were visualized with an Olympus AX70 Provis microscope equipped with epifluorescence and the cells on each slide were counted with ImagePro-plus program. The viability of cells after 24 hours in culture was analyzed by their ability to exclude trypan blue.

BrdU-labeling of the epithelial cell clusters remained low with or without GDNF, indicating that GDNF does not primarily act as a mitogen upon the ureteric epithelial cells. This result was verified by counting the number of bud cells immediately after the microdissection from the embryo and after 24 hours of hanging drop culture with or without GDNF or HGF (FIG. 4). Most cells in control, GDNF- and HGF-supplemented cultures were viable after 24 hours and excluded trypan blue. Cells from TGFβ1 cultures were not counted because of the total dissociation and extensive death of cells seen with TGFβ1. The results in FIG. 4 show that, without a proper mesenchymal support, neither GDNF nor HGF promoted proliferation of ureteric cells.

A well-known culture model for epithelial morphogenesis is the branching growth of MDCK cell cysts in collagen matrices enriched with HGF (Montesano et al., 1991a). To compare the behavior of normal ureteric buds with that of the MDCK cells, we cultured isolated ureteric buds with or without GDNF and HGF in rat tail collagen gel, as described for MDCK epithelial cells (Montesano et al., 1991a). Rat tail collagen gels were prepared essentially as described by Montesano et al. (1991b). Briefly, 8 volumes of collagen stock solution was mixed with 1 volume of 10 x concentrated MEM, 10% of FBS, and 1 volume of sodium bicarbonate (11.76 mg/ml), the mixture being kept on ice to prevent gelation. 200 μl of the control or growth factor-containing (50 ng/ml of GDNF or HGF) mixture was added to each well of the Nunclon 24-well culture dish and separated $E_r13$ ureteric buds without metanephric mesenchyme were pipetted on to the gel. An additional 100 μl of the collagen mixture was placed on top of the tissues, and after gelation was complete a further 200 μl MEM with 10% FCS was added. During five days of culture, tissues were photographed each day under an Olympus phase contrast ZDH10 microscope. Neither of these growth factors induced branching of the ureteric epithelium under these conditions.

Example 4

Downregulation of GDNF expression and ureteric branching after desulphation of extracellular matrix glycosaminoglycans Present and previous work on ureteric bud development indicated that the processes of growth and branching may be controlled separately (Davies et al., 1995). Both can be inhibited completely when kidney rudiments are deprived of sulphated glycosaminoglycans (S-GAGs), by treatment with either chlorate ions (inhibitors of sulphation) or degradative enzymes such as heparitinase and chrondroitinase, and they can be rescued apparently independently when these S-GAG deprive rudiments are treated with exogenous factors. HGF will restore growth but not branching and, while no growth factor that can rescue branching has yet been reported, treatment of S-GAG deprived kidneys with the phorbol ester, phorbal 12-myristate 13-acetate (PMA), will activate branching but not growth (Davies et al., 1995). We used the following protocols to determine whether GDNF can activate ureteric bud growth, branching or both in S-GAG deprived kidneys.

To inhibit the sulphation of extracellular matrix sulphated GAGs, $E_m11$ kidneys were cultured and treated with chlorate as described by Davies et al. (1995). The medium of some cultures was supplemented with one of the following: a) 20 mM NaClO3 (BDH AnaLaR 10435); b) 50 ng/ml GDNF; c) 20 mM NaClO3 plus 50 ng/ml GDNF; d) 20 mM NaClO3 plus 100 ng/ml HGF; e) 20 mM NaClO3 plus 50 ng/ml GDNF plus 100 ng/ml HGF. Kidney rudiments were left to develop in these media for approximately 72 hours, then fixed for whole-mount immunohistochemistry and stained with antibodies against the collecting-duct specific stain anti-calbindin-D-28k. Alternatively, $E_r13$ dissected rat kidneys were cultured as described, and heparitinase III (Sigma) and chondroitinase ABC (Sigma) were added to the culture medium at 0.33 U/ml each as described (Davies et al., 1995). The culture medium was changed daily with fresh enzymes. At the second day of the culture, either GDNF- or BSA-soaked agarose beads were added next to ureters and Wolffian ducts, and tissues were cultured for additional two days, and were then processed for whole-mount immunohistochemistry and Western blotting analysis.

Sets of 12 kidneys, grown for 55 hours in medium described above as well as without 20 mM NaClO3, were homogenised in 100 μl of 2-mercaptoethanol-containing Laemmli sample buffer (Biorad), then their proteins were separated by SDS-PAGE (12.5% gel) and blotted on to Biorad transfer membranes. After transfer, membranes were washed in PBS, blocked in 1% Blocking agent (Amersham RPN 3023 in PBS for 3 hours at room temperature, then incubated overnight at +4° C. in 0.5 μg/ml primary antibody (either chick anti-GDNF, Promega, or rabbit anti cRet, Santa Cruz) in PBS. They were then washed in 1% blocking agent and incubated in 1:400 secondary antibody (fluorescein anti-rabbit or fluorescein anti-chicken, Sigma) for 3 hours at room temperature. After another wash, filters were probed with tertiary antibody (alkaline phosphatase anti-fluorescein, Amersham) in 100 mM Tris, 400 mM NaCl pH 7.5 for 2 hours at room temperature. They were then washed extensively and developed using the NBT/BCPIP reagent from Amersham's RNA Colour Kit (RPN3300). Molecular weights were measured against pre-stained molecular weight standards (Biorad).

Figure 5A:
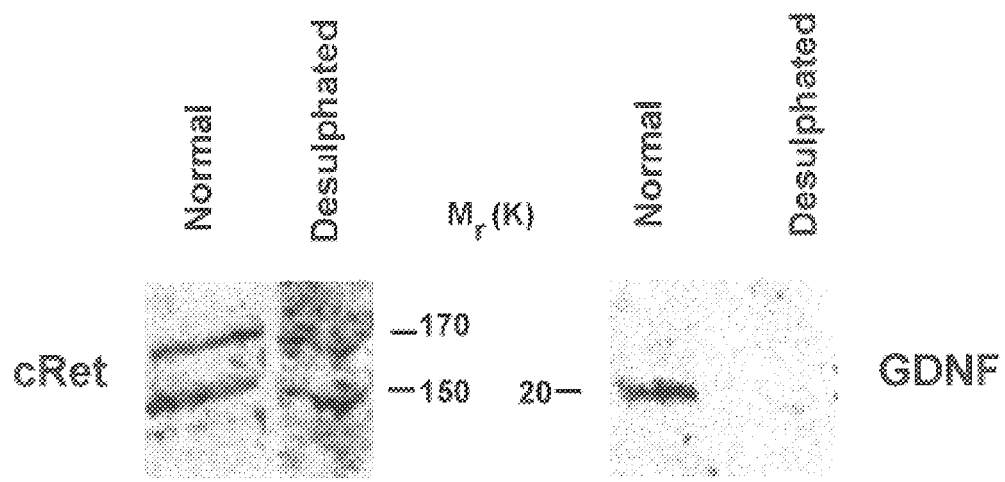
FIGS. 5A–E. Induction of branching by GDNF in desulphated kidneys where normal branching is disrupted. All explants were cultured for 3 days. Markers for ureteric buds and Wolfflan duct: calbindin-D-28k (B, C, and D) and L1 neural cell adhesion molecule (E).
A. Western blotting analysis with antibodies against mouse cRet and GDNF shows that GDNF (right), but not cRet (left), is down-regulated in desulphated kidneys treated in chlorate. B. With desulphation ureteric branching morphogenesis is disrupted. C. 50 ng/ml GDNF promotes short branches in desulphated kidneys. D. A kidney with desulphation and 50 ng/ml GDNF and 100 ng/ml HGF. E. A desulphated kidney grown with GDNF-soaked agarose bead. Note that two nearby branches are directed towards the bead. ub=ureteric bud, mes=metanephric mesenchyme, Wd=Wolffian duct. Bar: 250 μm.
Figure 5B:
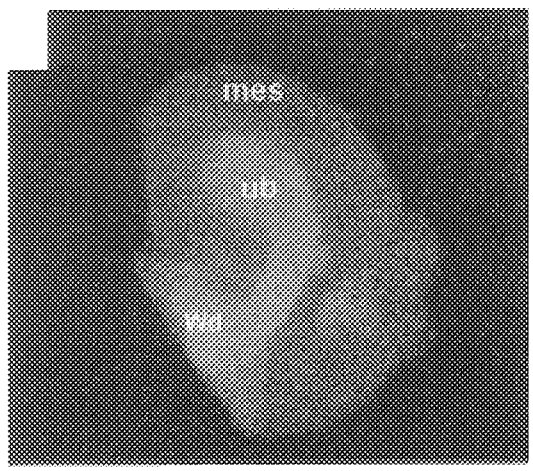
Figure 5C:
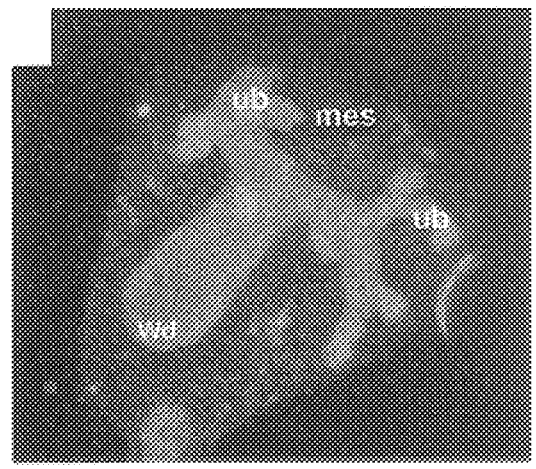
Figure 5D:
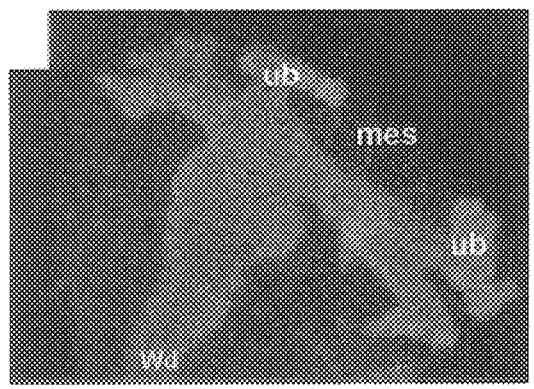
Figure 5E:
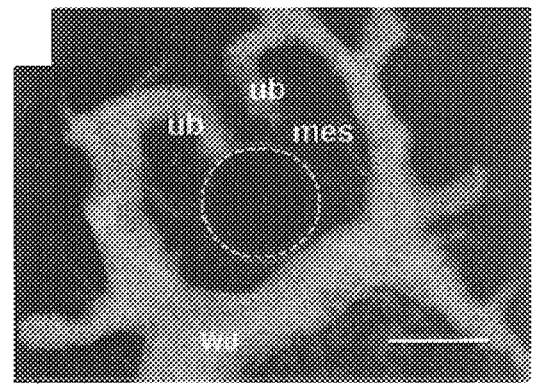

GDNF, but not cRet, was downregulated in desulphated kidneys as shown by Western blotting analysis (FIG. 5A). Ureteric epithelia of kidneys deprived of S-GAGs, through growth in desulphating media, showed neither extensive growth nor branching (FIG. 5B). Treatment of S-GAG deprived kidney rudiments with 50 ng/ml HGF stimulated ureteric growth but not branching, as shown earlier (Davies et al., 1995). Addition of GDNF partially restored the morphogenesis of ureteric buds, causing branching but only little growth (FIG. 5C). Simultaneous treatment of S-GAG deprived rudiments with 50 ng/ml GDNF and 100 ng/ml HGF did not extend significantly the effect that was seen with GDNF along (FIG. 5D). When the GDNF-containing beads were used in desulphated kidneys, branching was slightly more extensive than with GDNF added in the medium and the branches were often directed towards the bead (FIG. 5E). Beads soaked in 1% BSA showed no effect.

Example 5

Branching of early ureter bud in recombination cultures

Thus far, the only embryonic mesenchymes that have been reported to support growth and branching of ureteric bud epithelium have been metanephrogenic (Grobstein, 1955; Saxén, 1987) and lung mesenchymes (Kispert et al., 1996). To discover if this specificity is mediated by GDNF, we tested the effects of GDNF on early bud-stage $E_r13$ rat ureteric epithelium that was recombined with undifferentiated heterologous mesenchymes from embryonic mouse or rat lung, salivary gland, limb bud, tooth or gut, following the procedure disclosed in Example 2 above.

Figure 6A:
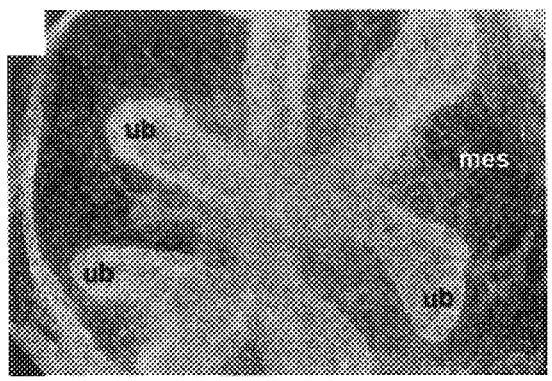
FIGS. 6A–E. The effects of GDNF and HGF on ureteric branching in $E_r13$ ureteric bud-heterologous mesenchyme explants. Cell-type markers: laminin (A, B, C and E) and DB-lectin (D). A. Lung mesenchyme-ureteric epithelium recombination after 48 hours in culture with 50 ng/ml GDNF shows extensive ureteric branching. Note that no secondary branches are seen. B. Similar explant with 50 ng/ml HGF. C. Lung mesenchyme-ureter bud recombination without exogenous growth factors shows no branches. D. Limb mesenchyme-ureteric bud recombination with 50 ng/ml GDNF. E. Salivary mesenchyme-ureteric bud recombination with 50 ng/ml GDNF. ub=ureteric bud, mes=mesenchyme. Bar 200 μm.
Figure 6B:
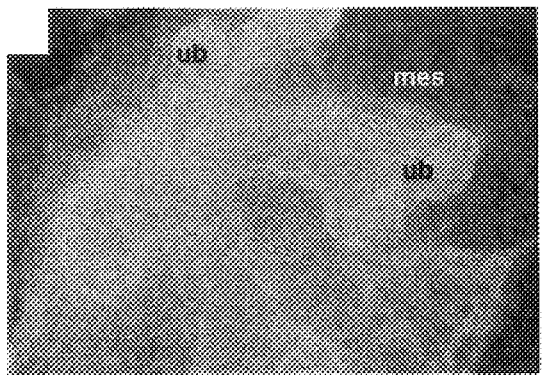
Figure 6C:
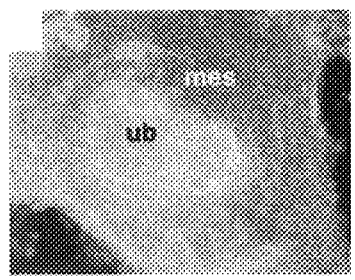

When recombined with lung mesenchyme, which expresses GDNF mRNA when tested by RT-PCR and GDNFR-$\alpha$ by in situ hybridization, Suvanto et al. 1997), the ureteric bud branched in a manner that correlated with the dose of exogenous GDNF (Table 1, FIG. 6A). Also, exogenous TGF$\beta$1 and HGF added to the culture medium of ureteric bud-lung mesenchyme recombinations triggered branching (Table 1, FIGS. 6B, C). If the ureteric epithelium was microdissected later, at the T-bud-stage when the first two ureteric branches were already present, and recombined with $E_r13$ lung mesenchyme, ureteric branching was regularly promoted without any exogenous growth factors (see Kispert et al., 1996).

Figure 6D:
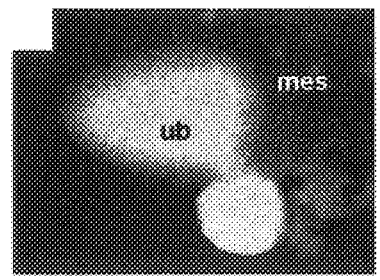
Figure 6E:
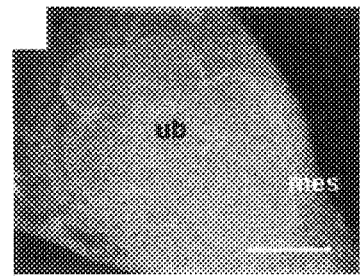

When $E_r13$ ureteric buds were recombined with isochronic mesenchymes from limb or tooth, the buds did not branch even if treated with GDNF, TGFA$\beta$1, or HGF. In limb mesenchyme recombinations the ureteric bud did not form branches with or without exogenous growth factors (FIG. 6D). In salivary gland mesenchyme recombinations, the ureteric buds maintained a rudimentary epithelial shape but did not elongate (FIG. 6E). Because gut is a rich source of GDNF (Hellmich et al., 1996; Suvanto et al., 1996), various segments and sizes of gut mesenchyme were recombined with ureteric buds, but they did not promote ureteric bud branching, not even if exogenous (GDNF up to 50 ng/ml was added. All these mesenchymes express GDNFR-$\alpha$ mRNA by in situ hybridization Suvanto et al., 1997). Branching of the late T-bud-stage ureteric epithelium was not supported by these heterologous mesenchymes either.

Example 6

Method for treating diseases

GDNF can be administered to patients with Hirschsprung's disease or renal dysplasia. The dosages are expected to be those effective to prevent apoptosis of enteric neuronS—in the case of Hirschsprung's disease—and kidney cells—in the case of renal dysplasia. Of course, the appropriate dosage depends upon numerous factors, such as the progression of the disease, patient status, etc. However, proper dosages are readily determined by persons of ordinary skill in the art. It is contemplated that an effective dose will fall in the range of from about 10 ng/kg/day to about 10 $\mu$g/kg/day.

The foregoing examples are meant to illustrate the invention and do not limit it in any way. Other applications and modifications are within the spirit and scope of the invention as herein disclosed and will be readily apparent to those skilled in the art.

The references cited herein are listed below.

REFERENCES

Affolter, M., Nellen, D., Nussbaumer, U. and Basle, K. (1994). Multiple requirements for the receptor serine/threonine kinase thick veins reveal novel functions of TGF-beta homologs during Drosophila embryogenesis. *Development* 120, 3105–3107

Arenas, E., Trupp, M., Åkerund, P., Ibáñez, C. (1995). GDNF prevents degeneration and promotes the phenotype of brain noradrenergic neurons in vivo. *Neuron* 15, 1465–1473.

Baloh, R. H., Tansey, M. G., Golden, J. P., Creedon, D. J., Heuckeroth R. O., Keck, C. L., Zimonjic D. B., Popescu, N. C., Johnson Jr., E. M. and Milbrandt, J. (1997). TrnR2, a novel receptor that mediated neurturin and GDNF signaling through ret. *Neuron* 18, 793–802.

Buj-Bello, A., Buchman, V. L., Horton, A., Rosenthal, A. and Davies, A. M. (1995). GDNF is an age-specific survival factor for sensory and autonomic neurons. *Neuron* 15, 821–828.

Davies, J. A., Lyon, M., Gallagher, J. and Garrod. D. (1995). Sulphated proteoglycan is required for collecting duct growth and branching but not nephron formation during kidney development. *Development* 121, 1507–1517.

Dudley, A. T., Lyons, K. M. and Robertson, E. (1995). A requirement for bone morphogenetic protein-7 during development of the mammalian kidney and eye. *Genes Devel.* 9, 2795–2807.

Durbec, P., Marcos-Gutierrez, V., Kilkenny, C., Grigoriou, M., Wartiovaara, K., Suvanto, P., Smith, D., Ponder, B., Costantini, F., Saarma, M., Sariola, H. and Pachnis, V. (1996). GDNF signalling through the Ret receptor tyrosine kinase. *Nature (London)* 381, 789–793.

Ebendal, T., Tomac, A., Hoffer, B. J. and Olson, L. (1995). Glial cell line-derived neurotrophic factor stimulates fiber formation and survival in cultured neurons from peripheral autonomic ganglia. *J. Neurosci. Res.* 40, 276–284.

Ekblom, P., Miettinen, A. and Saxén, L. (1980). Induction of brush border antigens of the proximal tubule in the developing kidney. *Devel. Biol.* 74, 263–274.

Ekblom, P., Thesleff, I., Saxén, L., Miettinen, A. and Timpl, R. (1983). Transferrin as a fetal growth factor: acquisition of responsiveness related to embryonic induction. *Proc. Natl. Acad. Sci. (USA)* 80, 2651–2655.

Grobstein, C. (1953). Inductive epithelio-mesenchymal interaction in cultured organ rudiments of the mouse. *Science* 118, 52–55.

Grobstein, C. (1955). Inductive interaction in the development of the mouse metanephros. *J. Exp. Zool.* 130, 319–339.

Hellmich, H. L., Kos, L., Cho, E. S., Mahon, K. A. and Zimmer, A. (1996). Embryonic expression of glial cell-line derived neurotrophic factor (GDNF) suggests multiple developmental roles in neural differentiation and epithelial-mesenchymal interactions. *Mech. Devel.* 54, 95–105.

Henderson, C. E., Phillips, H. S. Pollack, R. A., Davies, A. M., Lemeulle, C., Armanini, M., Simmons, L., Moffet, B., Vandlen, R.A., Simmons, L. et al. (1994). GDNF: a potent survival factor for motomeurons present in peripheral nerve and muscle. *Science* 266, 1062–1064.

Jing, S., Wen, D., Yu, Y., Holst, P. L., Luo, Y., Fang, M., Tamir, R., Antonio, L., Hu, Cupples, R. et al (1996). GDNF-induced activation of the Ret protein tyrosine kinase is mediated by GDNFR-a, a novel receptor for GDNF. *Cell* 85, 9–20.

Kispert, A., Vainio, S., Shen, L. Y., Rowitch, D. H. and McMahon, A. P. (1996). Protcoglycans are required for maintenance of Wnt-11 expression in the ureter tips. *Development* 122, 3627–3637.

Kotzbauer, P. T., Lampe, P. A., Heuckeroth, R. O., Golden, J. P., Creedon, D. J., Johnson, E. M., Milbrandt, J. D. (1996) Neuturin, a relative of glial-cell-line-derived neurotrophic factor. *Nature* 384, 467–470.

Kreidberg, J., Sariola, H., Loring, J., Maeda, M., Pelletier, J., Housman, D. and Jaenicsh, R. (1993). WT-1 is required for early kidney development. *Cell* 74, 679–69.

Lin, L. -F. H., Doherty, D. II., Lile, J. D., Bektesh, S. and Collins F. (1993). GDNF: a glial cell line-derived neurotrophic factor for midbrain dopaminergic neurons. *Science* 260, 1130–1132.

Liu, Z. Z., Wada, J., Kumar, A., Carone, F. A., Takahaski, M. and Kanwar Y. S. (1996). Comparative role of phosphotyrosine kinase domains of c-ros and c-ret protooncogenes in metanephric development with respect to growth factors and matrix morphogens. *Devel. Biol.* 178, 133–148.

Luo, G., Hofmann, C., Bronckers, A. L. J. J., Sohocki, M., Bradley, A. and Karsenty, G. (1995). BMP-7 is an inducer of nephrogenesis, and is also required for eye development and skeletal patterning. *Genes Devel.* 9, 2808–2820.

Miller, J. and Moon, R. (1996). Signal transduction through β-catenin and specification of cell fate during embryogenesis. *Genes Devel.* 10, 2527–2539.

Montesano, R., Matsumoto, K., Nakamura T. and Orci, L. (1991a). Identification of a fibroblast-derived epithelial morphogen as hepatocyte growth factor. *Cell* 67, 901–908.

Montesano, R., Schaller, G., and Orci, L. (1991b). Induction of epithelial tubular morphogenesis in vitro by fibroblast-derived soluble factors. *Cell* 66, 697–711.

Olive, S., Dubois, C., Schachner, M. and Rougon, G. (1995). The F3 neuronal glycosylphosphatidylinositol-linked molecule is localized to gylcolipid-enriched membrane subdomains and interacts with L1 and fyn kinase in mouse cerebellum. *J. Neurochem.* 65, 2307–2317.

Oppenheim, R. W., Houenou, L. J., Johnson, J. E., Lin, L. F., Li, L., Lo, A. C., Newsome, A. L., Prevette, D. M. and Wang, S. (1995). Developing motor neurons rescued from programmed and axotomy-induced cell death by GDNF. *Nature (London)* 373, 344–346.

Pachnis, V., Mankoo, B. and Constantini, F. (1993). Expression of the cRet protooncogene during mouse embryogenesis. *Development* 119, 1005–1017.

Partanen, A. -M. and Thesleff, I. (1987). Localization and quantitation of $125_I$ epidermal growth factor binding in mouse embryonic tooth and other embryonic tissues at different developmental stages. *Devel. Biol.* 120, 186–197.

Perantoni, A., Dove, L. and Karavanova, I. (1995). Basic fibroblast growth factor can mediate the early inductive events in renal development. *Proc. Natl. Acad. Sci. (USA)* 92, 4696–4700.

Pichel, J. G., Shen, L., Sheng, H. Z., Granholm, A-C., Drago, J., Grinberg, A., Lee, E. J., Huang, S. P., Saarma, M., Hoffer, B. J., Sariola, Hr. and Westphal, H. (1996). Defects in enteric innervation and kidney development in mice lacking GDNF. *Nature (London)*, 382, 73–76.

Rathjen, F. and Schachner, M. (1984). Immunocytological and biochemical characterization of a new neuronal cell surface component (L1 antigen) which is involved in cell adhesion. *EMBO J* 3, 1–10.

Reichman-Fried, M. and Shilo B. Z. (1995). Breathless, a Drosophila FGF receptor homolog, is required for the onset of tracheal cell migration and tracheole formation. *Mech. Devel.* 52, 265–273.

Richter, A., Sanford, K. and Evan, V. (1972). Influence of oxygen and culture media on plating efficiency of some mammalian tissue cells. *J. Natl. Cancer Inst.* 49, 1705–1712.

Ritvos, O., Tuuri, T., Erämaa, M. Sainio, K., Hildén, K., Saxén, L. and Gilbert, S. (1995). activin disrupts epithelial branching morphogenesis in developing glandular organs of the mouse. *Mech. Devel.* 50, 229–245.

Sainio, K., Hellstedt, P., Kreidberg, J. A., Saxén, L. Sariola, H. (1997). Differential regulation of two sets of mesonephric tubules by WT-1. *Development* 124, 1293–1299.

Sainio, K., Nonclercq, D., Saarma, M., Palgi, J., Saxén, L. and Sariola, H. (1994). Neuronal characteristics in embryonic renal stroma. *Int. J. Dev. Biol.* 38, 77–84.

Sánchez, M. P., Silos-Santiago, I., Frisén, J., He, B., Lira, S. A. and Barbacid, M. (1996). Renal agenesis and the absence of enteric neurons in mice lacking GDNF. *Nature (London)* 382, 70–73.

Santoro, M., Wong, W. T., Aroca, P., Santos, E., Matoskova, B., Grieco, M., Fusco, A. and di Fiore, P. P. (1994). An epidermal growth factor receptor/ret chimera generates mitogenic and transforming signals: evidence for a ret-specific signaling pathway. *Molec. Cell. Biol.* 14, 663–675.

Santos, O. F. P., Barros, E. J. G., Yang, Z. -M., Matsumoto, K., Nakamura, T., Park, M. and Nigam, S. K. (1994). Involvement of hepatocyte growth factor in kidney development. *Devel. Biol.* 163, 525–529.

Sariola, H. Holm, K. and Henke-Fahle, S. (1988). Early innervation of the metanephric kidney. *Development* 104, 589–599.

Saxén, L. (1987). Organogenesis of the kidney. Cambridge University Press, Cambridge.

Saxén, L. and Lehtonen, E. (1987). Embryonic kidney in organ culture. *Differentiation* 36, 2–11.

Schmidt, C., Bladt, F. goedecke, S., Brinkman, V., Zschiesche W., Sharpe M., Gherardi, E. and Birchmeier, C. (1995). Scatter factor/hepatocyte growth factor is essential for liver development. *Nature (London)* 373, 699–702.

Schuchardt, A., D'Agati, V., Pachnis, V. and Costantini, F. (1996). Renal agenesis and hypodysplasia in ret-k- mutant mice result from defects in ureteric bud development. *Development* 122, 1919–1929.

Schuchardt, A., D'Agati, V., Larsson-Blomberg, L., Constantini, F. and Pachnis, V. (1994). Defects in the kidney and enteric nervous system of mice lacking the tyrosinc kinase receptor Ret. *Nature (London)* 367, 380–383.

Schull, M. M. Ormsby, I., Kier, A. B., Pawlowski, S., Diebold, R. J., yin, M., Alle, R., Sidman, C., Proetzel, G., Calvin, D. et al. (1992). Targeted disruption of the mouse transforming growth factor-beta 1 gene results in multifocal inflammatory disease. *Nature (London)* 359, 693–699.

Stark, K., Vainio, S., Vassileva, G. and McMahon, A. P. (1994). Epithelial transformation of metanephric mesenchyme in the developing kidney regulated by Wnt-4. *Nature (London)* 372, 679–683.

Suvanto, P., Hiltunen, J. O. Arumäe, U., Moshnyakov, M., Sariola, H., Sainio., K. and Saarma, M. (1995). Localization of glial cell line-derived neurotrophic factor (GDNF) and mRNA in embryonic rat by in situ hybridization. *Eur. J. Neurosci.* 8, 816–822.

Suvanto, P., Wartiovaara, K., Lindahl, M., Arumäu, U., Moshnyakov, M., Horelli-Kuitunen, N., Airaksinen, M. S., Palotie, A., Sariola, H. and Saarma M. (1997) Cloning, mRNA distribution and chromosomal localization of the gene for glial cell line-derived neurotrophic factor receptor beta, a homologue to GDNFR-alpha. *Hum. Mol. Gen.* 6, in press.

Takahaski, M., Buma, Y., Iwamoto, T., Inaguma, Y., Ikeda, H. and Hiai, H. (1988). ret transforming gene encodes a fusion protein homologous to tyrosine kinases. *Mol. Cell Biol.* 7, 1378–1385.

Takeichi, M. (1993). Cadherins in cancer: implications for invasion and metastasis. *Curr. Opin. Cell Biol.* 5, 806–811

Tomac, A., Lindqvist, E., Lin, L. -F. H., Ögren, S. O. Young, D., Hoffer, B. J. and Olson, L. (1995). Protection and repair of the nigrostriatal dopaminergic system by GDNF in vivo. *Nature (London)* 373, 335–339.

Torres, M., Gómez-Pardo, E., Dressler, G. and Gruss, P. (1995). Pax-2 controls multiple steps of urogenital development. *Development* 121, 4057–4065.

Treanor, J. J., Goodman, L., de Sauvage, F., Stone, D. M., Poulsen, K. T., Beck, C. D., Gray, C., Armanini, M. P. Pollock, R. A., Hefti, F. et al. (1996). Characterization of a multicomponent receptor for GDNF. *Nature (London)* 382, 80–83.

Trupp, M., Arenas, E., Fainzilber, M., Nilsson, A. -S., Sieber, B. -A., Grigoriou, M., Kilkenny, C., Salazar-Grueso, E., Pachnis, V., Arumäc, U. et al. (1996). Functional receptor for GDNF encoded by the cRet proto-oncogene. *Nature (London)* 381,785–789.

Uemura, T., Oda, H., Kraut, R., Hayaski, S., Kotaoka, Y. and Takeichi, M. (1996) Zygotic Drosophila E-cadherin expression is required for processes of dynamic epithelial cell rearrangement in the Drosophila embryo. *Genes Devel.* 10, 659–671.

Vainio, S., Karavanova, I., Jowett, A. K. and Thesleff, I. (1993). Identification of BMP-4 as a signal mediating secondary induction between epithelial and mesenchymal tissues during early tooth development. *Cell* 75, 45–58.

Vega, Q. C., Worby, C. A., Lechner, M. S. Dixon, J. E. and Dressler, G. R. (1996). Glial cell line-derived neurotrophic factor activates the receptor tyrosine kinase ret and promotes kidney morphogenesis. *Proc. Natl. Acad. Sci. (USA)* 93, 10657–10661.

Virtanen, I., Miettinen, M., Lento, V. -P., Kariniemi, A. -L- and Passivuo, R. (1985). Diagnostic applications of monoclonal antibodies to intermediate filaments. *Ann. N.Y. Acad. Sci.* 455, 635–648.

Vukicevic, S., Kopp, J. B., Luyten, F. P. and Kuber Sampath, T. (1996). Induction of nephrogenic mesenchyme by osteogenic protein 1 (bone morphogenetic protein 7). Proc. Natl. Acad. Sci. (USA) 93, 9021–9026.

Wilkinson, D. and Green, P. (1990). In situ hybridization and the three-dimensional reconstruction of serial sections. In: *Postimplantation Mammalian Embryos. A Practical Approach.* (ed. A. Copp and D. Cockroft). pp 155–171. Oxford University Press: London.

Woolf, A. S., Kolatsi-Joannou, M., Hardman, P., Andermarcher, E., Moorby, C., Fine, L. G., Jat, P. S. Noble, M. D. and Gherardi, E. (1995). Roles of hepatocyte growth factor/scatter factor and the met receptor in the early development of the metanephros. *J. Cell Biol.* 128, 171–184.

Worby, C. A., Vega, Q. C., Zhao, Y., Chao, H. H. -J., Seasholtz, A. F. and Dixon, J. E. (1996). Glial cell line-derived neurotrophic factor signals through the RET receptor and activates mitogen-activated protein kinase. *J. Biol. Chem.* 271, 23619–23622.

Wright, D. E. and Snider, W. D. (1996). Focal expression of glial cell line-derived neurotrophic factor in developing mouse limb bud. *Cell Tissue Res.* 286, 209–217.

Yan, Q., Matheson, C. and Lopez, O. T. (1995). In vivo neurotrophic effects of GDNF on neonatal and adult facial motor neurons. *Nature (London)* 373, 341–344.

All references cited herein are hereby incorporated by reference in their entireties.

TABLE 1

Dose response to GDNF, TGFβ1 an HGF in lung mesenchyme-ureteric bud recombination cultures. The number of samples in each concentration is 8.

| | Average number of branches | | | | |
|---|---|---|---|---|---|
| Concentration | 1 ng/ml | 10 ng/ml | 25 ng/ml | 50 ng/ml | 100 ng/ml |
| GDNF | 2 | 3 | 5 | 5 | 7 |
| HGF | 0 | 3 | 3 | 5 | 5 |
| TGFβ1 | 1 | 3 | 4 | 2 | 0 |

What is claimed is:

1. A method for maintaining ureteric cells in culture said method comprising culturing said ureteric cells in a medium containing glial cell line-derived neurotrophic factor (GDNF).

2. The method of claim 1 wherein the concentration of GDNF is from about 1 ng/ml to about 100 ng/ml.

3. The method of claim 1 wherein the ureteric cells are cultured as hanging drops.

4. The method of claim 1 wherein the ureteric cells are cultured in collagen gels.

5. A method for preventing apoptosis of ureteric cells said method comprising contacting said ureteric cells with glial cell line-derived neurotrophic factor (GDNF).

6. The method of claim 5 wherein the concentration of GDNF is from about 1 ng/ml to about 100 ng/ml.

7. A method for stimulating ureteric budding from the Wolffian duct in bud-negative metanephric mesenchymes said method comprising contacting said metanephric mesenchymes with glial cell line-derived neurotrophic factor (GDNF).

8. The method of claim 7 wherein the concentration of GDNF is from about 1 ng/ml to about 100 ng/ml.

9. The method of claim 7 wherein the concentration of GDNF is from about 50 ng/ml to about 100 ng/ml.

10. A method for stimulating ureteric branching from the Wolffian duct in bud-positive metanephric mesenchymes said method comprising contacting said metanephric mesenchymes with glial cell line-derived neurotrophic factor (GDNF).

11. The method of claim 10 wherein the concentration of GDNF is from about 1 ng/ml to about 100 ng/ml.

12. The method of claim 10 wherein the concentration of GDNF is from about 50 ng/ml to about 100 ng/ml.

13. A method for stimulating ureteric branching said method comprising culturing early bud-stage ureteric epithelium with lung mesenchymes in the presence of a growth factor selected from the group consisting of glial cell line-derived neurotrophic factor (GDNF), hepatocyte growth factor/scatter factor, and transforming growth factor-β1.

14. The method of claim 13 wherein the growth factor is GDNF.

15. The method of claim 13 wherein the concentration of GDNF is from about 1 ng/ml to about 100 ng/ml.

16. The method of claim 15 wherein the concentration of GDNF is from about 50 ng/ml to about 100 ng/ml.

17. A method for treating Hirschsprung's disease or renal dysplasia said method comprising application of an amount of glial cell line-derived neurotrophic factor (GDNF) effective to prevent cellular apoptosis.

18. A method for stimulating axonal outgrowth said method comprising contacting neuroblasts with glial cell line-derived neurotrophic factor (GDNF).

19. The method of claim 18 wherein the concentration of GDNF is from about 1 ng/ml to about 100 ng/ml.

20. The method of claim 18 wherein the concentration of GDNF is from about 50 ng/ml to about 100 ng/ml.

21. A method for stimulating adhesion between ureteric cells said method comprising contacting said cells with glial cell line-derived neurotrophic factor (GDNF).

22. The method of claim 21 wherein the concentration of GDNF is from about 1 ng/ml to about 100 ng/ml.

23. The method of claim 21 wherein the concentration of GDNF is from about 50 ng/ml to about 100 ng/ml.

24. A method for stimulating the synthesis of basil lamina on ureteric cells said method comprising contacting said cells with glial cell line-derived neurotrophic factor (GDNF).

25. The method of claim 24 wherein the concentration of GDNF is from about 1 ng/ml to about 100 ng/ml.

26. The method of claim 24 wherein the concentration of GDNF is from about 50 ng/ml to about 100 ng/ml.

\* \* \* \* \*